US011090088B2

(12) United States Patent
Biedermann et al.

(10) Patent No.: US 11,090,088 B2

(45) Date of Patent: Aug. 17, 2021

(54) POLYAXIAL BONE ANCHORING DEVICE AND SYSTEM INCLUDING AN INSTRUMENT AND A POLYAXIAL BONE ANCHORING DEVICE

(71) Applicant: BIEDERMANN TECHNOLOGIES GMBH & CO. KG, Donaueschingen (DE)

(72) Inventors: Lutz Biedermann, VS-Villingen (DE); Timo Biedermann, Trossingen (DE); Bernd Fischer, Bräunlingen (DE)

(73) Assignee: BIEDERMANN TECHNOLOGIES GMBH & CO. KG, Donaueschingen (DE)

( * ) Notice: Subject to any disclaimer, the term of this patent is extended or adjusted under 35 U.S.C. 154(b) by 216 days.

(21) Appl. No.: 16/287,896

(22) Filed: Feb. 27, 2019

(65) Prior Publication Data

US 2019/0274737 A1 Sep. 12, 2019

Related U.S. Application Data

(60) Provisional application No. 62/639,224, filed on Mar. 6, 2018.

(30) Foreign Application Priority Data

Mar. 6, 2018 (EP) .................................... 18160167

(51) Int. Cl.

| | |
|---|---|
| ***A61B 17/70*** | (2006.01) |
| *A61B 17/56* | (2006.01) |
| *A61B 90/00* | (2016.01) |

(52) U.S. Cl.

CPC ...... *A61B 17/7037* (2013.01); *A61B 17/7032* (2013.01); *A61B 17/7035* (2013.01);

(Continued)

(58) Field of Classification Search

CPC .................. A61B 17/70; A61B 17/7032–7046

See application file for complete search history.

(56) References Cited

U.S. PATENT DOCUMENTS

| | | | |
|---|---|---|---|
| 5,217,497 | A | 6/1993 | Mehdian |
| 5,375,956 | A | 12/1994 | Pennig |

(Continued)

FOREIGN PATENT DOCUMENTS

| | | | |
|---|---|---|---|
| EP | 2 462 886 | A1 | 6/2012 |
| EP | 2 574 297 | A1 | 4/2013 |

(Continued)

OTHER PUBLICATIONS

Extended European Search Report for Application No. 18160167.5, dated Aug. 30, 2018, 10 pages.

(Continued)

*Primary Examiner* — Eduardo C Robert
*Assistant Examiner* — Michelle C Eckman
(74) *Attorney, Agent, or Firm* — Lewis Roca Rothgerber Christie LLP

(57) ABSTRACT

A polyaxial bone anchoring device includes a receiving part with an upper member having a first end, a second end, and a recess at the first end for receiving a rod, and a lower member connectable around the second end of the upper member, and a pressure member positionable in the upper member to exert pressure on a head of a bone anchoring element. The lower member is movable from a first position where the head is pivotable, to a second position closer to the first end of the upper member where an angular position of the head is locked while the recess remains vacant or unobstructed. When the lower member is at the second position, at least part of the lower member is aligned axially with at least part of an end face at the second end of the upper member.

25 Claims, 16 Drawing Sheets

(52) U.S. Cl.
CPC ..... *A61B 17/7076* (2013.01); *A61B 2017/564* (2013.01); *A61B 2090/037* (2016.02)

(56) References Cited

U.S. PATENT DOCUMENTS

| | | | | |
|---|---|---|---|---|
| 5,549,608 | A | 8/1996 | Errico | |
| 5,575,792 | A | 11/1996 | Errico | |
| 5,586,984 | A | 12/1996 | Errico | |
| 5,672,176 | A | 9/1997 | Biedermann et al. | |
| 5,728,098 | A | 3/1998 | Sherman et al. | |
| 5,882,350 | A | 3/1999 | Ralph et al. | |
| 6,063,090 | A | 5/2000 | Schläpfer | |
| 6,248,105 | B1 | 6/2001 | Schläpfer | |
| 6,254,602 | B1 | 7/2001 | Justis | |
| 6,273,888 | B1 | 8/2001 | Justis | |
| 6,299,616 | B1 | 10/2001 | Beger | |
| 6,582,436 | B2 | 6/2003 | Schlapfer et al. | |
| 6,743,231 | B1 | 6/2004 | Gray et al. | |
| 7,316,684 | B1 | 1/2008 | Baccelli et al. | |
| 7,947,065 | B2 | 5/2011 | Hammill, Sr. | |
| 7,955,359 | B2 | 6/2011 | Matthis et al. | |
| 7,967,826 | B2 | 6/2011 | Colleran et al. | |
| 7,988,694 | B2 | 8/2011 | Barrus et al. | |
| 8,075,603 | B2 | 12/2011 | Hammill, Sr. | |
| 8,298,275 | B2 | 10/2012 | Rezach | |
| 8,506,609 | B2 | 8/2013 | Biedermann et al. | |
| 8,506,610 | B2 | 8/2013 | Biedermann | |
| 8,636,781 | B2 | 1/2014 | Biedermann | |
| 9,005,260 | B2 | 4/2015 | Dauster et al. | |
| 9,050,148 | B2 | 6/2015 | Jackson | |
| 9,060,814 | B2 | 6/2015 | Doubler et al. | |
| 9,144,441 | B2 | 9/2015 | Biedermann et al. | |
| 9,173,684 | B2 | 11/2015 | Biedermann et al. | |
| 9,333,016 | B2 | 5/2016 | Biedermann et al. | |
| 9,681,895 | B2 | 6/2017 | Biedermann et al. | |
| 9,895,171 | B2 | 2/2018 | Webb | |
| 2004/0254576 | A1 | 12/2004 | Dunbar, Jr. et al. | |
| 2005/0080415 | A1 | 4/2005 | Keyer et al. | |
| 2005/0096653 | A1 | 5/2005 | Doubler et al. | |
| 2005/0228385 | A1 | 10/2005 | Iott | |
| 2006/0036252 | A1 | 2/2006 | Baynham et al. | |
| 2006/0074445 | A1 | 4/2006 | Gerber et al. | |
| 2006/0111715 | A1 | 5/2006 | Jackson | |
| 2006/0173454 | A1 | 8/2006 | Spitler et al. | |
| 2006/0241600 | A1 | 10/2006 | Ensign et al. | |
| 2006/0247631 | A1 | 11/2006 | Ahn et al. | |
| 2006/0247658 | A1 | 11/2006 | Pond | |
| 2007/0043358 | A1 | 2/2007 | Molz, IV et al. | |
| 2007/0123862 | A1 | 5/2007 | Warnick | |
| 2007/0161987 | A1 | 7/2007 | Capote | |
| 2007/0191835 | A1* | 8/2007 | Justis ................. | A61B 17/7035 606/279 |
| 2007/0233078 | A1 | 10/2007 | Justis et al. | |
| 2007/0270842 | A1 | 11/2007 | Bankoski | |
| 2008/0015576 | A1 | 1/2008 | Whipple | |
| 2008/0015579 | A1 | 1/2008 | Whipple | |
| 2008/0045963 | A1 | 2/2008 | Abdou | |
| 2008/0108992 | A1 | 5/2008 | Barry et al. | |
| 2008/0161859 | A1 | 7/2008 | Nilsson | |
| 2008/0208256 | A1 | 8/2008 | Thramann | |
| 2009/0036934 | A1 | 2/2009 | Biedermann et al. | |
| 2009/0062860 | A1 | 3/2009 | Frasier | |
| 2009/0105715 | A1 | 4/2009 | Belliard | |
| 2009/0105756 | A1 | 4/2009 | Richelsoph | |
| 2009/0149887 | A1 | 6/2009 | Schlaepfer et al. | |
| 2010/0030135 | A1 | 2/2010 | Mitchell | |
| 2010/0036433 | A1 | 2/2010 | Jackson | |
| 2010/0131017 | A1 | 5/2010 | Farris et al. | |
| 2010/0160977 | A1 | 6/2010 | Gephart et al. | |
| 2010/0168796 | A1 | 7/2010 | Eliasen et al. | |
| 2010/0168800 | A1 | 7/2010 | Biedermann et al. | |
| 2010/0204735 | A1 | 8/2010 | Gephart et al. | |
| 2011/0060374 | A1 | 3/2011 | Sicvol et al. | |
| 2011/0125196 | A1 | 5/2011 | Quevedo et al. | |
| 2011/0208248 | A1 | 8/2011 | Barrus et al. | |
| 2011/0276098 | A1 | 11/2011 | Biedermann et al. | |
| 2012/0046699 | A1 | 2/2012 | Jones et al. | |
| 2012/0059426 | A1 | 3/2012 | Jackson | |
| 2012/0095516 | A1 | 4/2012 | Dikeman | |
| 2012/0179209 | A1 | 7/2012 | Biedermann et al. | |
| 2012/0197314 | A1 | 8/2012 | Farris | |
| 2012/0203288 | A1 | 8/2012 | Lange et al. | |
| 2012/0209332 | A1 | 8/2012 | Janowski | |
| 2012/0209335 | A1 | 8/2012 | Termyna et al. | |
| 2012/0310284 | A1 | 12/2012 | Gerchow | |
| 2013/0053901 | A1 | 2/2013 | Cormier et al. | |
| 2013/0085536 | A1 | 4/2013 | Biedermann et al. | |
| 2013/0096623 | A1 | 4/2013 | Biedermann et al. | |
| 2013/0110179 | A1 | 5/2013 | Barrus et al. | |
| 2013/0110180 | A1 | 5/2013 | Doubler et al. | |
| 2013/0123860 | A1 | 5/2013 | Biedermann et al. | |
| 2013/0123861 | A1 | 5/2013 | Biedermann et al. | |
| 2013/0150852 | A1* | 6/2013 | Shluzas .............. | A61B 17/7035 606/65 |
| 2014/0012337 | A1* | 1/2014 | Biedermann ........ | A61B 17/844 606/328 |
| 2014/0031880 | A1 | 1/2014 | Biedermann et al. | |
| 2014/0214097 | A1 | 7/2014 | Jackson et al. | |
| 2015/0119940 | A1 | 4/2015 | Jackson et al. | |
| 2015/0134006 | A1 | 5/2015 | Ziolo et al. | |
| 2015/0182265 | A1 | 7/2015 | Biedermann et al. | |
| 2015/0250512 | A1* | 9/2015 | Poker ................. | A61B 17/7037 606/305 |
| 2016/0030090 | A1 | 2/2016 | Webb | |
| 2016/0220281 | A1 | 8/2016 | Biedermann et al. | |
| 2017/0020574 | A1 | 1/2017 | Biedermann et al. | |
| 2018/0036039 | A1 | 2/2018 | Biedermann et al. | |
| 2018/0055542 | A1 | 3/2018 | Biedermann | |

FOREIGN PATENT DOCUMENTS

| | | | |
|---|---|---|---|
| EP | 3 120 791 | A1 | 1/2017 |
| EP | 3 184 063 | A1 | 6/2017 |
| JP | 2007-506525 | A | 3/2007 |
| WO | WO 2005/030070 | A1 | 4/2005 |
| WO | WO 2011/043799 | A1 | 4/2011 |
| WO | WO 2011/077511 | A1 | 6/2011 |
| WO | WO 2012/088890 | A1 | 7/2012 |
| WO | WO 2015/069873 | A1 | 5/2015 |

OTHER PUBLICATIONS

Extended European Search Report for Application No. 17198406.5, dated May 7, 2018, 9 pages.

European Search Report for European Application No. 16182818.1, European Search Report dated Jan. 18, 2017 and dated Jan. 25, 2017 (8 pages).

Extended European Search Report for European Application No. 12174846.1, European Search Report dated Nov. 7, 2012 and dated Nov. 14, 2012 (6 pgs.).

Search of the Austrian Patent Office by Serv.ip, “Ihr Partner für Forschung und Innovation Express-Recherche zum Stand der Technik,” dated Aug. 8, 2012, 6 pp.

* cited by examiner

POLYAXIAL BONE ANCHORING DEVICE AND SYSTEM INCLUDING AN INSTRUMENT AND A POLYAXIAL BONE ANCHORING DEVICE

CROSS-REFERENCE TO RELATED APPLICATION(S)

The present application claims priority to and the benefit of U.S. Provisional Patent Application No. 62/639,224, filed Mar. 6, 2018, the contents of which are hereby incorporated by reference in their entirety, and claims priority from European Patent Application EP 18 160 167.5, filed Mar. 6, 2018, the contents of which are hereby incorporated by reference in their entirety.

BACKGROUND

The application relates to a polyaxial bone anchoring device and a system including a polyaxial bone anchoring device and an instrument for use with the device. More specifically, the bone anchoring device includes a receiving part for coupling a rod to a bone anchoring element and a pressure member for exerting pressure onto an inserted head of the bone anchoring element. The receiving part includes an upper member and a lower member that can be mounted together to clamp the head.

DESCRIPTION OF RELATED ART

WO 2011/077511 A1 describes a spine fixing device capable of being used as both a pivotable type and a fixed type. The spine fixing device is provided with a screw and a head to which the screw and the rod can be fixed. The head is provided with a head body and a fixing nut which fixes the screw at a screw disposing section of the head body. The state of mounting of the fixing nut to the head body is adapted to be switchable between a first state in which the screw is able to pivot and a second state in which the screw is not able to pivot.

U.S. Pat. No. 9,333,016 B2 describes a polyaxial bone anchoring device including an anchoring element and a receiving part for coupling the anchoring element to a rod, wherein the receiving part includes an upper member, a lower member, and a clamping member at or near a bottom end of the upper member. When the head is inserted and the lower member screwed towards the upper member the head abuts against a stop in the upper member so that the head is held by friction in an adjustable angular position in the receiving part. A pressure member is also provided that transfers the pressure exerted by the locking screw via the rod onto the head for locking the head.

SUMMARY

In spinal surgery, often multiple segments of the spinal column have to be corrected and/or stabilized using a spinal rod and polyaxial bone anchoring devices. During such a procedure, repeated adjustments of bone anchoring elements and the rod relative to receiving parts of the polyaxial bone anchoring devices may become necessary.

It is therefore an object of the invention to provide a further improved polyaxial bone anchoring device that allows for safe and convenient handling during surgery, and to provide a system including such a polyaxial bone anchoring device and an instrument adapted for use therewith.

More generally, according to an embodiment, the polyaxial bone anchoring device includes a receiving part having an upper member and a lower member connectable to the upper member, the lower member including a seat for a head of a bone anchoring element, the receiving part further including a pressure member for exerting pressure onto an inserted head. When the lower member is connected to the upper member, the lower member can assume a first position in which an inserted had is pivotable and a second position in which the inserted head is clamped between the lower member and the pressure member.

By moving the lower member, more particularly, by rotating the lower member relative to the upper member, the locking and unlocking of the head can be effected, for example using an instrument. The lower member remains in a locking position even after removing the instrument. Locking of the head is achieved by clamping with such a force that the head is not able to pivot under operating conditions.

The locking and unlocking of the head during surgery can also be carried out with the rod not yet inserted or being at an elevated position in the receiving part away from the bottom of the rod receiving recess. This increases the possibilities of carrying out correction steps during surgery.

Moreover the locking and unlocking of the head can be effected independently from the fixation of the rod. Hence, the locking of the head can be maintained while adjustments on the position of the rod can be made.

When the head of the bone anchoring element is locked in the receiving part and the rod is still movable, it is possible to pull the bone anchoring device with the instrument towards the inserted rod, thereby also pulling the associated vertebra towards the rod for correcting a position of the vertebra. Therefore, the polyaxial bone anchoring device permits various adjustments and re-adjustments of the angular position and/or rod position during surgery.

The polyaxial bone anchoring device can also include frictional clamping of the head in the receiving part that allows to temporarily hold the bone anchoring element in an adjustable angular position of the head prior to the final locking of the bone anchoring device.

Legs of the upper member may each include a separable portion that forms extended tabs. The extended tabs allow convenient manipulation of the polyaxial bone anchoring device during surgery. Furthermore, the extended tabs permit guiding and/or supplying elements of an implant or instruments to the implantation site. This is particularly useful in the case of minimally-invasive surgery (MIS). The extended tabs may be broken off after locking the head and the rod.

According to one embodiment, the polyaxial bone anchoring device may be used in a pre-assembled manner, with the bone anchoring element being pre-assembled with the receiving part before inserting the bone anchoring element into bone. In another embodiment, the polyaxial bone anchoring device may be a bottom-loading bone anchoring device in which the bone anchoring element is inserted from the bottom into the receiving part. This allows for placing the bone anchoring element into the bone first, and thereafter mount the receiving part. By means of this, a modular system may be provided that allows combining of various anchoring elements with the receiving part on demand, depending on the actual clinical requirements.

BRIEF DESCRIPTION OF THE DRAWINGS

Further features and advantages of the invention will become apparent from the description of embodiments by means of the accompanying drawings. In the drawings.

DETAILED DESCRIPTION

Figure 1:
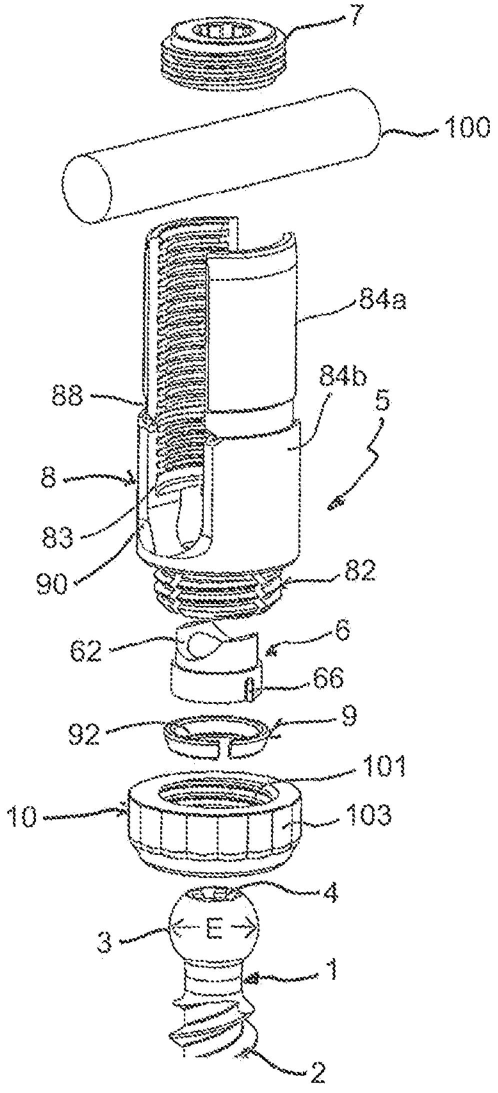
FIG. 1 shows a perspective exploded view of a polyaxial bone anchoring device according to a first embodiment.
Figure 2:
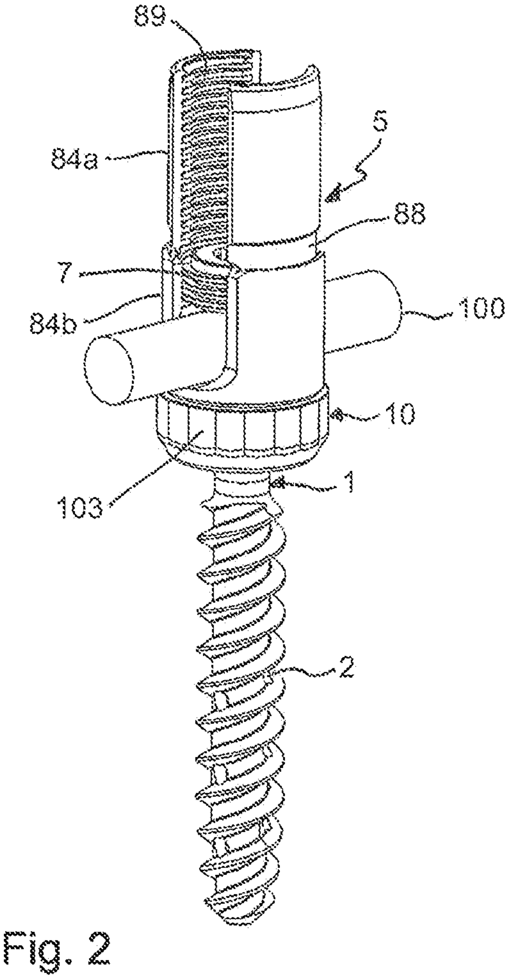
FIG. 2 shows a perspective view of the polyaxial bone anchoring device of FIG. 1 in an assembled state.
Figure 3:
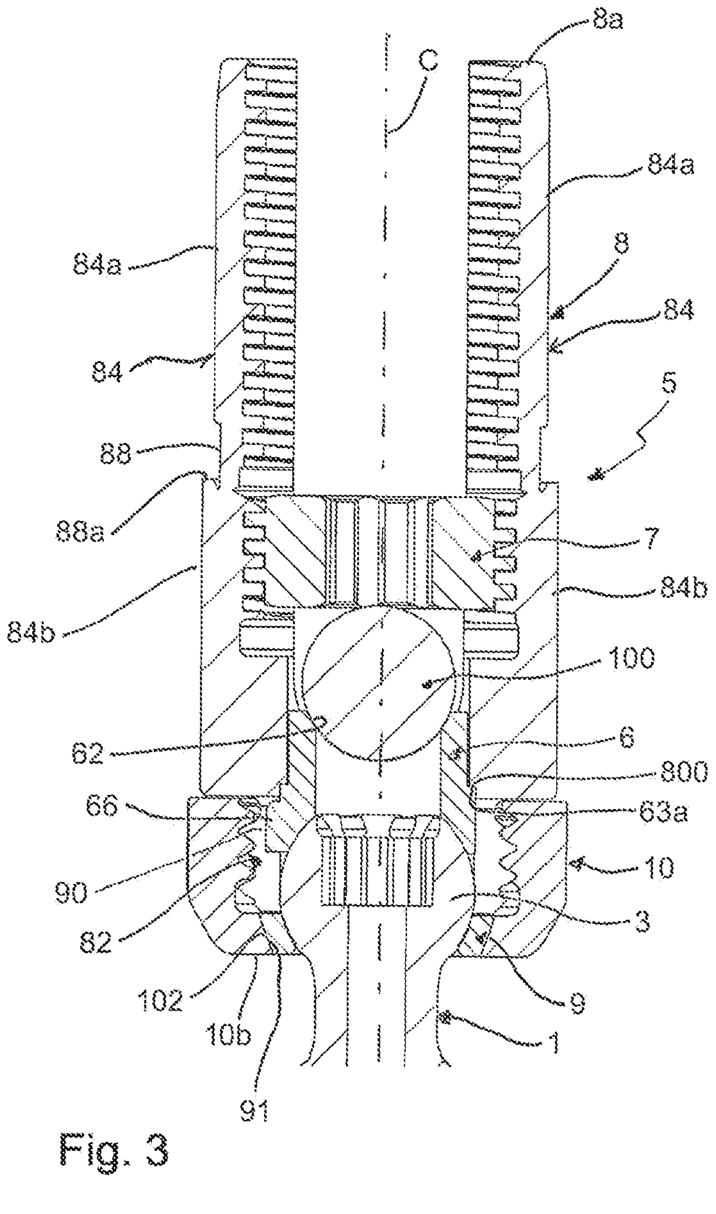
FIG. 3 shows a cross-sectional view of the polyaxial bone anchoring device of FIGS. 1 and 2 in an assembled state, the cross-section taken in a plane perpendicular to an axis of an inserted rod.
Figure 4:
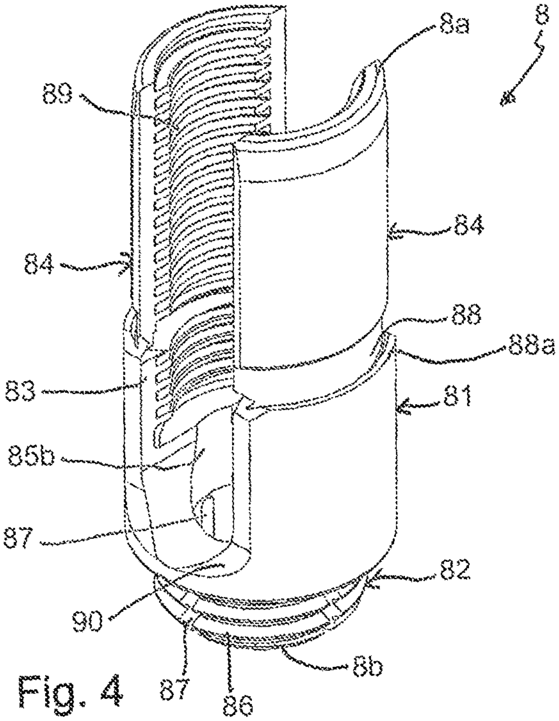
FIG. 4 shows a perspective view from a top of an upper member of a receiving part of the polyaxial bone anchoring device of FIGS. 1 to 3.
Figure 5:
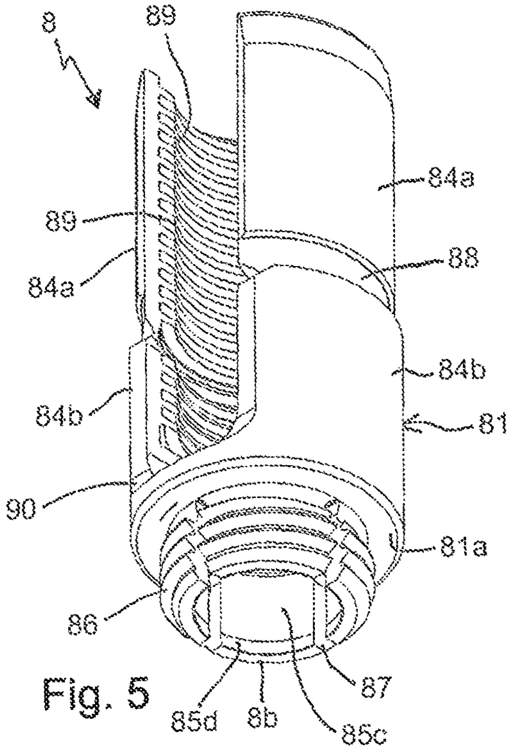
FIG. 5 shows a perspective view from a bottom of the upper member of FIG. 4.
Figure 6:
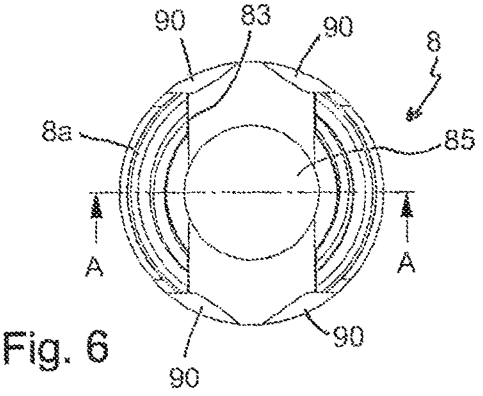
FIG. 6 shows a top view of the upper member of FIGS. 4 and 5.
Figure 7B:
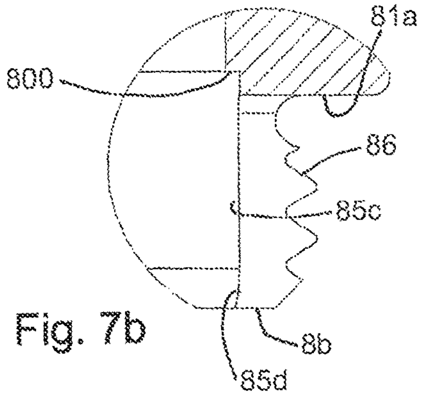
FIG. 7*b* shows an enlarged view of a detail of FIG. 7*a;*
Figure 7A:
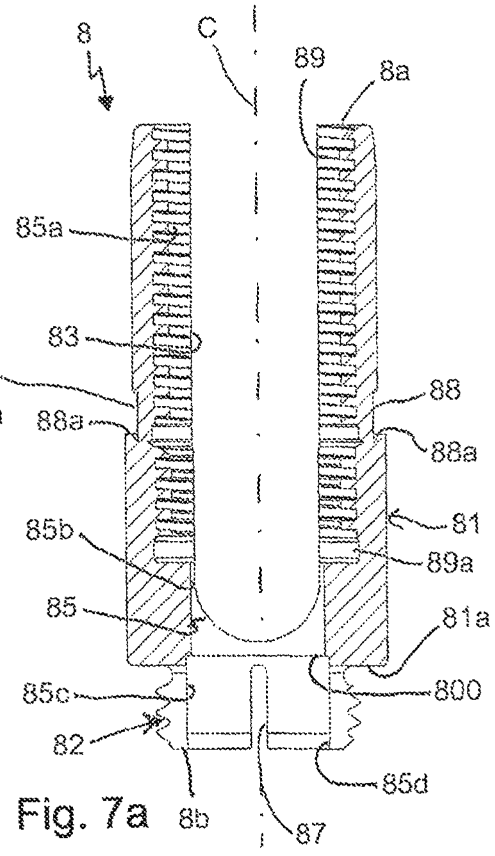
FIG. 7*a* shows a cross-sectional view of the upper member of FIGS. 4 to 6, the cross-section taken along line A-A in FIG. 6.
Figure 8:
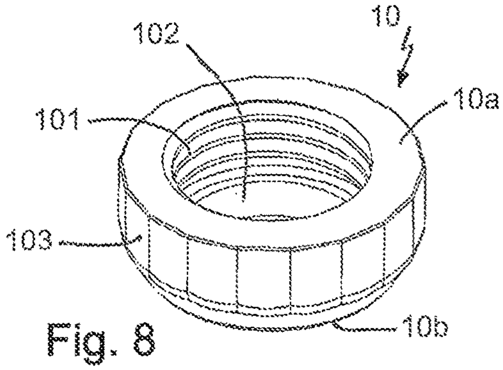
FIG. 8 shows a perspective view from a top of a lower member of the receiving part of the polyaxial bone anchoring device of FIGS. 1 to 3.
Figure 9:
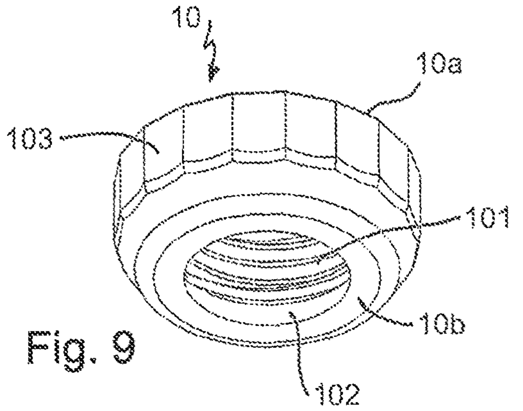
FIG. 9 shows a perspective view from a bottom of the lower member of FIG. 8.
Figure 10:
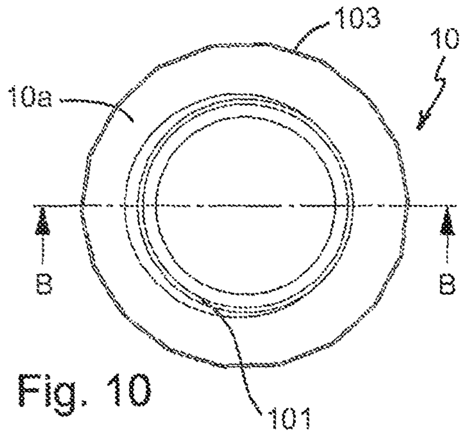
FIG. 10 shows a top view of the lower member of FIGS. 8 and 9.
Figure 11:
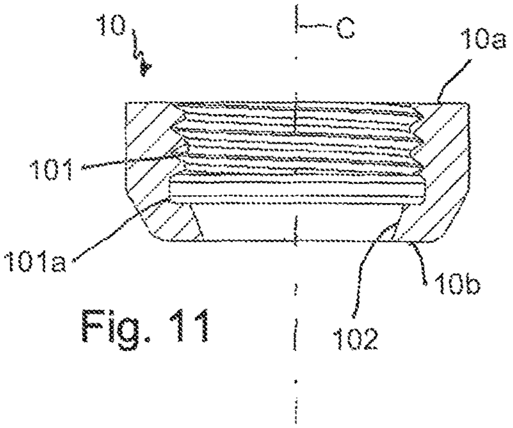
FIG. 11 shows a cross-sectional view of the lower member of FIGS. 8 to 10, the cross-section taken along line B-B in FIG. 10.

As shown in FIGS. 1 to 3, a polyaxial bone anchoring device according to a first embodiment includes a bone anchoring element 1 in the form of a bone screw having a shank 2 with a threaded portion and a head 3 having a spherically shaped outer surface portion. The head 3 has a largest diameter E and a recess 4 for engagement with a screwdriver at a free end surface. The bone anchoring device further includes a receiving part 5 for receiving the head of the anchoring element 1 and for receiving a rod 100 in order to couple the bone anchoring element 1 to the rod 100. In the receiving part 5, a pressure member 6 is arranged for exerting pressure onto the head 3 when the head 3 is inserted into the receiving part 5. In addition, the bone anchoring device includes a fixation element 7 for securing the rod 100 and for locking the head 3 in the receiving part 5.

As shown in FIG. 1, the receiving part 5 is a two part piece with an upper member 8 and a lower member 10 that is connectable to the upper member 8. Referring further to FIGS. 4 to 7*b*, the upper member includes a first end 8*a* forming an upper end and an opposite second end 8*b* forming a lower end. Due to its symmetry, the upper member 8 has a central axis C extending through the upper member 8 from the first end 8*a* to the second end 8*b*. Adjacent to the first end 8*a*, there is a first substantially cylindrical portion 81 with a first maximum outer diameter, and adjacent to the second end 8*b*, there is a second substantially cylindrical portion 82 with a second outer diameter that is smaller than the first outer diameter of the first portion 81. Thereby, a shoulder with a lower surface 81*a* is formed between the first portion 81 and the second portion 82. The first portion 81 of the upper member 8 has a substantially U-shaped recess 83 that extends from the first end 8*a* towards the second end 8*b* to a depth such that a bottom of the recess 83 is close to the junction between the first portion 81 and the second portion 82. By means of the substantially U-shaped recess 83, two upstanding free legs 84 are formed that are the sidewalls of a channel for receiving the rod 100.

The upper member 8 further has a coaxial passage 85 extending completely through the upper member 8 from the first end 8*a* to the second end 8*b*. The passage 85 may be a bore that may have different inner diameters along the axial direction. More specifically, the passage 85 may have a first portion 85*a* that extends from the first end 8*a* to a distance from the bottom of the substantially U-shaped recess 83, and that has a width sufficient to insert and advance the fixation member 7 therein. The passage 85 continues from the first portion 85*a* to a second portion 85*b* with a smaller width, wherein the second portion 85*b* is configured to receive a portion of the pressure member 6 in a sliding manner therein. The second portion 85*b* extends up to a short distance from the junction between the first portion 81 and the second portion 82 of the upper member 8. Adjacent to the second portion 85*b*, there is a third portion 85*c* of the passage 85 that has a greater diameter than the second portion 85*b* and that is configured to receive the head 3 therein. Hence, between the second portion 85*b* and the third portion 85*c* of the passage 85, a step is provided that forms a stop 800 for the pressure member 6, as explained below. Between the third portion 85*c* and the second end 8*b*, a spherically-shaped section 85*d* may exist and may be configured to match the outer spherical surface portion of the head 3, so as to accommodate and clamp a portion of the head 3 therein.

The second portion 82 of the upper member 8 includes at least in a section thereof an external thread 86 functioning as a advancement structure for advancing the lower member 10 over the upper member 8. A plurality of longitudinal slits 87 that extend substantially parallel to the central axis C are provided in the second portion 82. The slits 87 are preferably arranged at equidistant positions and are open towards the second end 8*b*. By means of the slits 87, the second portion 82 of the upper member 8 is rendered slightly expandable and compressible. This permits holding and clamping of an inserted head 3 by friction in the spherically-shaped section 85*d*, for example during assembly of the polyaxial bone anchoring device. The slits 87 are preferably arranged mirror symmetrical to a longitudinal axis of the U-shaped recess 83, in particular, two of the slits 87 are aligned with the U-shaped recess 83 and two others are 90° offset thereto.

At a distance from the first end 8*a*, a weakened section that permits breaking away or breaking off of a portion of the legs 84 is provided. The weakened section includes a circumferentially extending groove 88 on the outer surface of the upper member 8 that divides the legs 84 into a first or upper portion 84*a* extending above the groove 88 and a second or lower portion 84*b* extending below the groove 88 to a base of the recess 83. The lower wall of the groove projects beyond the upper wall in a radial direction, thereby forming a narrow shoulder 88*a*. At the groove 88, the wall thickness of the legs 84 is reduced. By means of this, the upper portions 84*a* form extended legs, also called extended tabs of the bone anchoring device. Such extended tabs may be particularly suitable to define a pathway, for example in minimally-invasive surgery (MIS) to guide an implant component, for example the fixation element 7, to the implantation site beneath the skin of the patient. Any other means for providing a weakened section for permitting breaking away of the upper portion 84*a* from the lower portion 84*b* may be contemplated, such as, for example, perforations, etc. In the region of the extended legs 84*a*, an outer diameter of the upper member 8 may be slightly smaller than an outer diameter of the region of the lower portion of the legs 84*b*. The free end of the lower portion of the legs forms the upper end of the receiving part 5 after breaking-off of the extended legs 84*a*.

An internal thread 89 is provided along at least part of the upper portion 84*a* and at least part of the lower portion 84*b* of the legs 84, so that the fixation element 7 can be screwed down along the pathway defined by the first portion 85*a* of the passage 83. The depth of the substantially U-shaped recess 83 is such that when the rod 100 is placed into the recess 83 and the fixation member 7 is screwed between the legs 84, the fixation member 7 does not substantially protrude out of the upper member 8 when the upper portions 84*a* of the legs have been broken-off. At a lower end of the internal thread 89, an undercut 89*a* may be present.

At the outer surface of the first portion 81, to the left and the right of the U-shaped recess 83, cut-outs 90 may be formed that can be engaged by an instrument in order to hold the upper member 8 in a rotationally fixed manner.

Referring in particular to FIGS. 8 to 11, the lower member 10 is a nut-like part that has a first end 10*a* forming an upper end and a second end 10*b* forming a lower end, and a passage that extends fully from the first end 10*a* to the second end 10*b*. The passage has a first portion 101 with an internal thread so that the lower member 10 can be screwed onto the second portion 82 of the upper member 8. At the end of the threaded first portion 101, an undercut 101*a* may be provided. Between the first portion 101 and the second end 10*b*, there is a second portion 102 that is threadless and that narrows towards the second end 10*b*, conically in this specific example. By means of the second portion 102, a seat for the head 3 of the bone anchoring element 1 is formed. An inner diameter of the opening provided by the passage at the second end 10*b* is greater than a maximum outer diameter of the shank 2 of the bone anchoring element 1, so that the shank 2 can be passed through the opening.

The outer surface of the lower member 10 has an engagement structure 103 that may be, as shown, a plurality of flat portions, arranged for example in a polygonal manner, that can be gripped by hand, for example when mounting the lower member 10, or with an instrument, for example when the bone anchoring device is in use. The engagement structure 103 may have any other shape that is suitable to be engaged by an instrument.

As shown in FIGS. 2 and 3, when the lower member 10 is mounted to the upper member 8, a maximum outer diameter of the lower member 10 is the same or only slightly greater than a maximum outer diameter of the upper member 8. An axial height of the lower member 10 is such that the lower member 10 can accommodate the head 3 of the bone anchoring element when the lower member 10 is connected to the upper member 8 in a final configuration.

Figure 12:
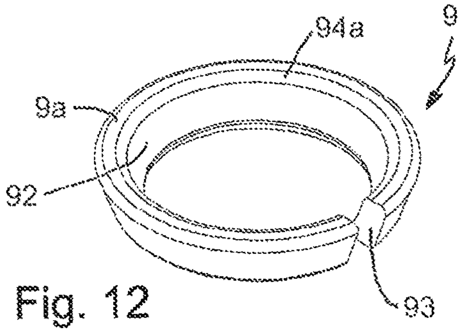
FIG. 12 shows a perspective view of an insert member of the receiving part of the polyaxial bone anchoring device of FIGS. 1 to 3.
Figure 13:
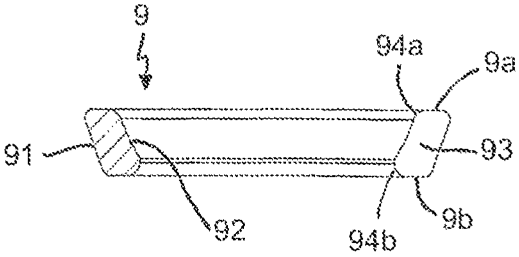
FIG. 13 shows a cross-sectional view of the insert member of FIG. 12.

Next, referring in more detail to FIGS. 12 and 13, in the lower member 10, a ring-shaped insert member 9 is provided for narrowing the opening at the second end 10*b* of the lower member 10. The insert member 9 has a first end 9*a* or upper end and a second end 9*b* or lower end. An outer surface 91 between the first end 9*a* and the second end 9*b* is tapered, for example conical, in a manner such that the insert member 9 fits into the narrowing second portion 102 of the lower member 10. An inner surface 92 of the ring-shaped insert member 9 has a spherical shape that is adapted to the shape of the spherical outer surface portion of the head 3. Hence, when the ring-shaped insert member 9 is mounted to the lower member 10, the inner surface 92 of the insert member 9 forms a seat for the head 3. The insert member 9 is slotted with a single slot 93 that renders the ring-shaped insert member 9 compressible, such that it can be mounted to the lower member 10 and held in the second portion 102 in a biased manner. Moreover, the ring-shaped insert member 9 may have a small bevelled inner surface portion 94*a* adjacent to the first end 9*a* and another small bevelled inner surface portion 94*b* adjacent to the second end 9*b*. It should be noted that the outer surface 91 can have a narrowing shape other than a conical shape, in particular a shape that is adapted to any narrowing surface of the second portion 102 of the passage in the lower member 10.

When the ring-shaped insert member 9 is mounted to the lower member 10, the opening provided by the passage at the second end 10*b* of the lower member is narrowed in such a manner that the head 3 cannot pass through the lower opening. The ring-shaped insert member 9 can be used when the maximum outer diameter of the shank 2 is greater than the maximum outer diameter E of the head 3. In such a case, the insert member 9 is mounted after passing the shank 2 through the passage.

Figure 14:
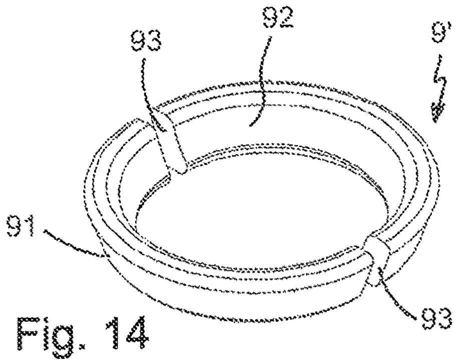
FIG. 14 shows a perspective view of another insert member that can be used in the polyaxial bone anchoring device of FIGS. 1 to 3.
Figure 15:
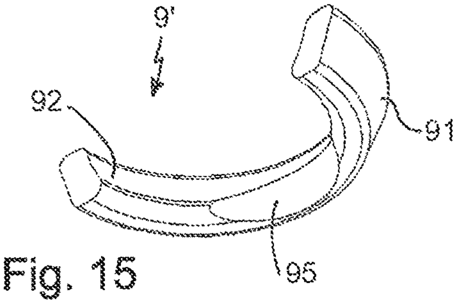
FIG. 15 shows a perspective view from a bottom of a modified portion of the insert member of FIG. 14.
Figure 16:
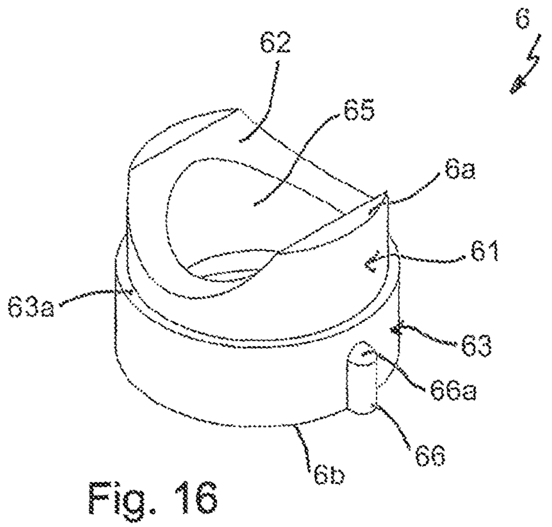
FIG. 16 shows a perspective view from a top of a pressure member of the polyaxial bone anchoring device of FIGS. 1 to 3.
Figure 17:
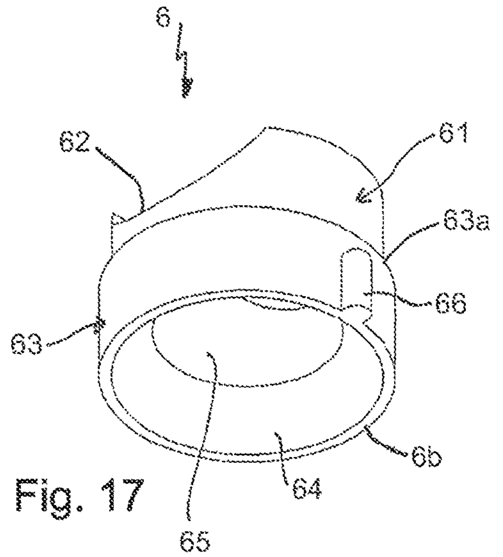
FIG. 17 shows a perspective view from a bottom of the pressure member of FIG. 16.

As shown in FIG. 14, a modified insert member 9' has two slots 93 extending completely through the insert member 9' and provided on diametrically opposite sides, such that the insert member 9' is a two-piece part. The modified insert member 9' can be used instead of the insert member 9. Referring to FIG. 15, the modified insert member 9' may have a recess or cut-out 95 that enlarges a space for pivoting of the shank 2 to a specific side. Thus, the maximum pivot angle to the side where the recess 95 is located is greater than in other pivot directions. More than one recess or cut-out to enlarge the pivot angle can also be provided at other circumferential locations to enlarge the pivot angle in other directions. Also, the ring-shaped insert member 9 according to FIGS. 12 and 13 can be provided with such a cut-out or recess 95.

Turning now to FIGS. 16 to 19, the pressure member 6 has a first end 6*a* or upper end and an opposite second end 6*b* or lower end. Adjacent to the first end 6*a*, the pressure member 6 has a first portion 61 that is substantially cylindrical with an outer diameter that is only slightly smaller than the inner diameter of the second portion 85*b* of the passage 85 in the upper member 8, so that the first portion 61 can slide in the second portion 85*b* of the passage 85. Perpendicular to a cylinder axis of the first portion, a substantially cylinder segment-shaped recess is formed that provides a rod support surface 62. Adjacent to the second end 6*b*, the pressure member 6 has a substantially cylindrical second portion 63 that has an outer diameter greater than that of the first portion 61. Hence, a shoulder 63*a* exists between the second portion 63 and the first portion 61. The shoulder 63*a* is configured to abut against the stop 800 in the upper member 8 of the receiving part 5 to limit an upward movement of the pressure member 6 towards the first end 8*a*. Adjacent to the second end 6*b*, there is a substantially spherical segment-shaped recess 64 with a radius corresponding to the radius of the head 3, so that when the pressure member 6 is placed onto the head 3 and presses onto the head, a load is distributed onto the head 3. Furthermore, a coaxial through-hole 65 is provided for allowing access to the recess 4 of the head 3.

Figure 18:
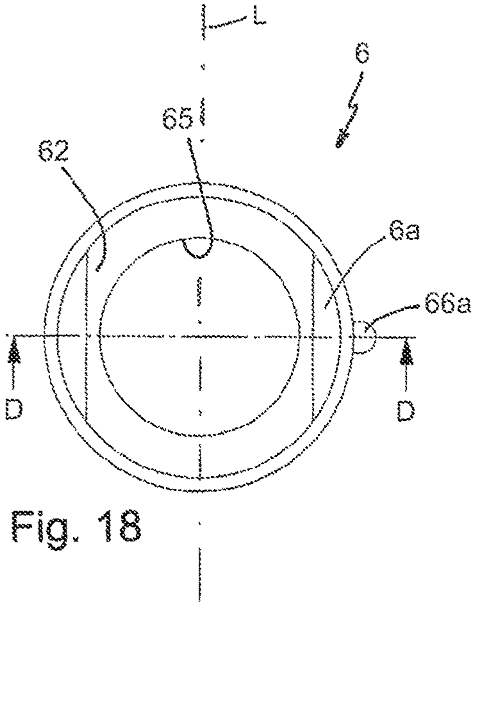
FIG. 18 shows a top view of the pressure member of FIGS. 16 and 17.
Figure 19:
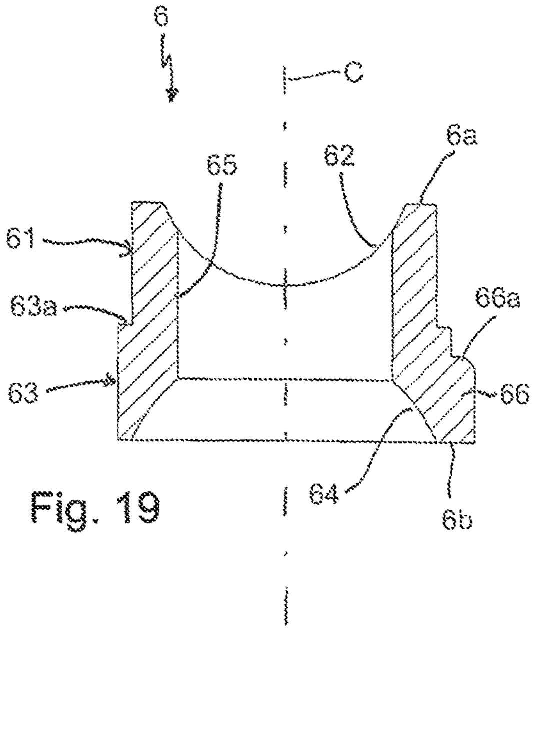
FIG. 19 shows a cross-sectional view of the pressure member of FIGS. 16 to 18, the cross-section taken along line D-D in FIG. 18.

As best seen in the top view of FIG. 18, at 90 degrees from an axis L corresponding to a cylinder axis of the rod support surface 62, a protrusion 66 is formed at the outer surface of the second portion 63. The protrusion 66 extends in an axial direction. It may have the shape of a semi-cylinder or be otherwise rounded with a rounded top portion 66*a*. The protrusion 66 is configured to engage one of the slits 87 in the second portion 82 of the upper member 8, so that the pressure member 6 is prevented from rotating. When the protrusion 66 engages one of the slits 87 that is 90° offset from the rod axis, the rod support surface 62 is aligned with the substantially U-shaped recess 83 so that the rod 100 can be placed.

The polyaxial bone anchoring device according to the first embodiment can be used in a pre-assembled manner. The shank 2 is passed through the passage in the lower member 10 so that the shank 2 goes through the opening at the second end 10*b*. Thereafter, the ring-shaped insert member 9 is inserted until it rests in the second portion 102 of the passage in the lower member 10. The pressure member 6 is mounted to the upper member 8 from the second end 8*b* of the upper member 8 and oriented in such a manner that the protrusion 66 can enter into one 90° off-set slit 87 to align the rod support surface 62 with the U-shaped recess 83. For mounting the lower member 10 to the upper member 8, the head 3 can be held by friction in the spherical portion 85*d* of the upper member 8. Then, the lower member 10 is screwed onto the second portion 82 of the upper member 8 until the head 3 rests in the seat 92. The head 3 is loosely held between the seat 92 and the pressure member 6 so that it is pivotable. If the largest external diameter of the shank is greater than or the same as the largest diameter E of the head 3, the above procedure may be used. If the largest diameter of the shank 2 is smaller than the largest diameter E of the head, the ring-shaped insert 9 may be mounted in the lower member 10 before the shank is passed through, or the ring-shaped insert 9 may be omitted altogether. In this case, the opening at the second end 10*b* is designed to be smaller than the largest diameter of the head.

Figure 20:
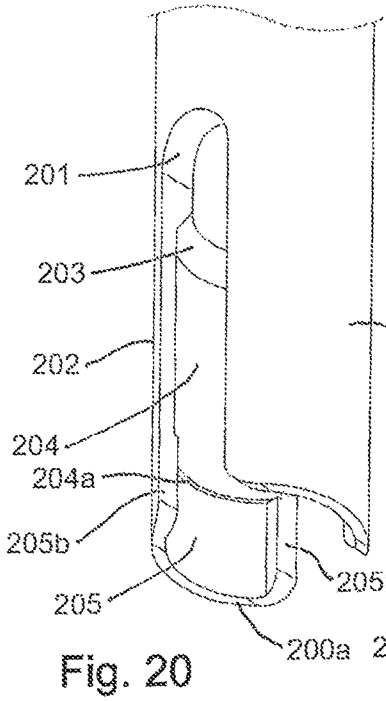
FIG. 20 shows a perspective view from a bottom of an inner sleeve of an instrument adapted to be used with the polyaxial bone anchoring device of FIGS. 1 to 3.
Figure 21:
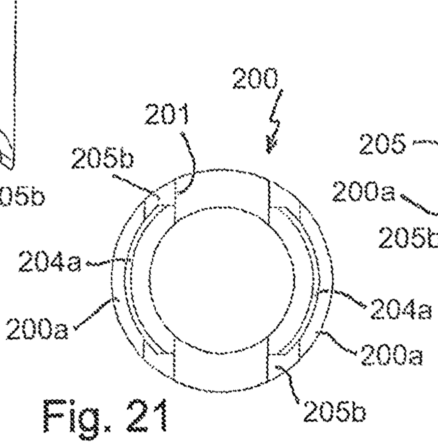
FIG. 21 shows a bottom view of the inner sleeve of FIG. 20.
Figure 22:
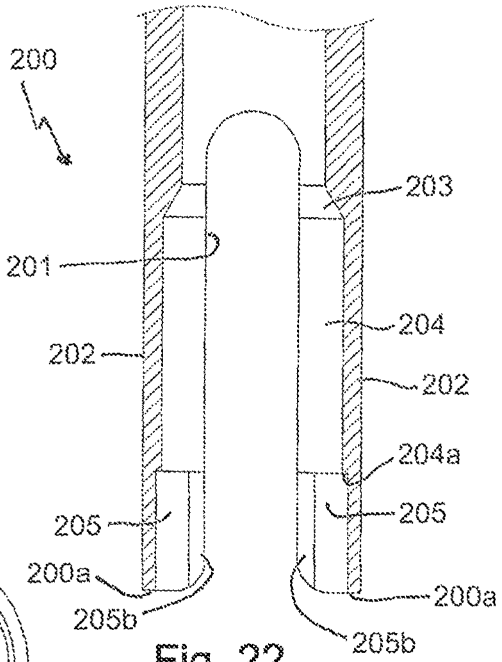
FIG. 22 shows a cross-sectional view of the inner sleeve of FIGS. 20 and 21.
Figure 23:
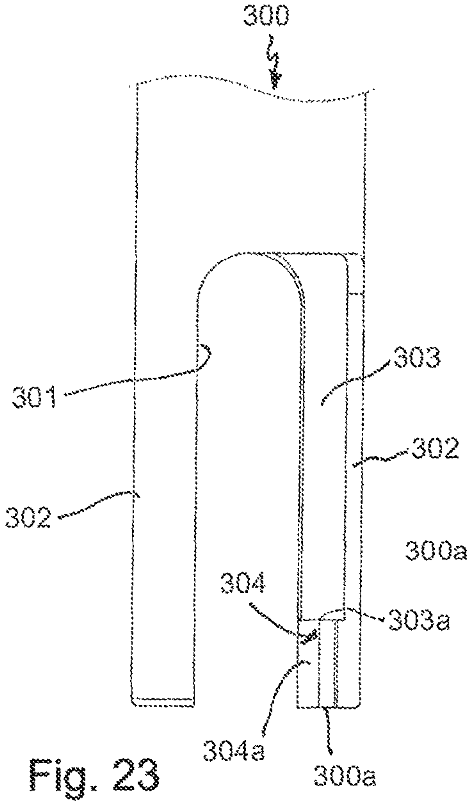
FIG. 23 shows a perspective view of an outer sleeve of the instrument adapted to be used with the polyaxial bone anchoring device of FIGS. 1 to 3.
Figure 24:
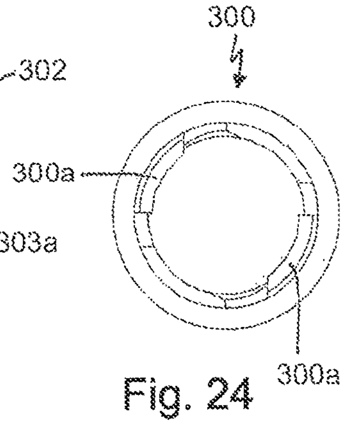
FIG. 24 shows a bottom view of the outer sleeve of FIG. 23.
Figure 25:
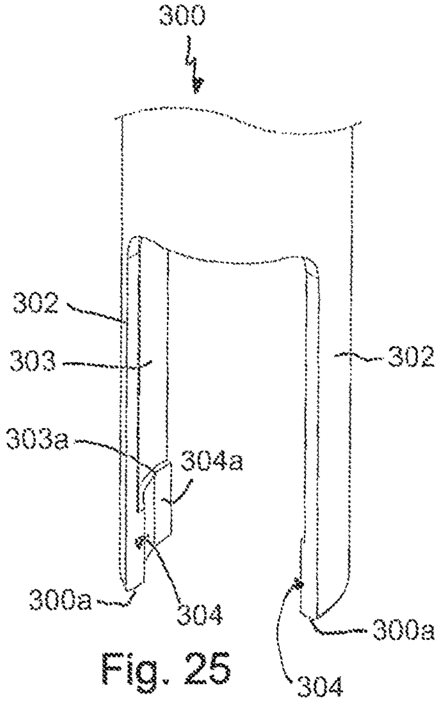
FIG. 25 shows a perspective view of a front portion of the outer sleeve of FIGS. 23 and 24.

Referring to FIGS. 20 to 25, an instrument will be described that is adapted for use with the polyaxial bone anchoring device. The instrument includes an inner sleeve 200 that is disposed in an outer sleeve 300. As shown in FIGS. 20 to 22, the inner sleeve has a front portion with a free end 200*a* and a substantially elongate recess 201 that divides the front portion into two opposite arms 202. The width of the elongate recess 201 is at least as large as the diameter of the rod 100. At a distance from the free end 200*a*, an inner taper 203 is provided that narrows the diameter from the front portion toward a rearward portion of the sleeve. Adjacent to the taper 203 in the direction to the free end 200*a*, an inner first sleeve portion 204 follows that is adapted to an outer shape of the upper portions 84*a* of the legs 84. The first portion 204 has an axial length such that it extends at least up to the circumferential shoulder 88*a* provided by the groove 88. The first sleeve portion 204 is followed by an inner second sleeve portion 205 with a slightly larger inner diameter so that a step 204*a* between the first sleeve portion 204 and the second sleeve portion 205 is formed and configured to rest on the projection 88*a* of the upper member 8. The second sleeve portion 205 has an inner diameter such that the lower portion 84*b* of the legs can be at least partially accommodated therein. Thickened side portions 205*b* are provided on each side of each of the arms 202 which side portions 205*b* are configured to engage the sides of the substantially U-shaped recess 83 in the upper member 8 at the positions of the cut-outs 90, respectively. Thereby, when the inner sleeve 200 is attached to the upper member 8, the upper member 8 is prevented from rotating relative to the inner sleeve 200. Moreover, the inner sleeve 200 is configured to receive a fixation member therethrough, so that the fixation member 7 can be moved down through the inner sleeve 200.

The outer sleeve 300 has a front portion with a free end 300*a*. A substantially rectangular recess 301 divides the front portion into two opposite arms 302. The width of the rectangular recess 301 is such that when the outer sleeve is placed onto the receiving part 5, the arms 302 can rotate to some extent before they abut against an inserted rod, as explained below. Hence, a width of the arms 302 in a circumferential direction is smaller than a width of the legs 84 of the upper member 8 in the circumferential direction.

The outer sleeve has an inner first sleeve portion 303 that extends up to a distance from the free end 300*a* and that has an inner diameter sufficient to accommodate the inner sleeve 200 therein. Following the first inner sleeve portion 303, there is an inner second sleeve portion 304 with an inner diameter smaller than the first inner sleeve portion, such that a shoulder 303*a* is formed between the first sleeve portion 303 and the second sleeve portion 304. In the mounted state, when the outer sleeve 300 is placed over the inner sleeve 200 and the instrument is attached to the polyaxial bone anchoring device, the second sleeve portion 304 encompasses the lower member 10 and the free end 200*a* of the inner sleeve abuts against the shoulder 303*a* of the outer sleeve 300 (see, e.g., FIG. 27*d*). The second sleeve portion 304 has a plurality of axially extending flat surfaces 304*a*, arranged in a polygonal manner, that are configured to engage the engagement structure in the form of the flat surfaces 103 of the lower member 10. Thereby, a form-fit engagement between the outer sleeve 300 and the lower member 10 is achieved that permits rotating of the lower member 10 with the outer sleeve 300 while the upper member 8 is rotationally fixed by the inner sleeve 200.

The parts of the polyaxial bone anchoring device and the instrument may each be made of a bio-compatible material, for example, of titanium or stainless steel, of a bio-compatible alloy, such as NiTi-alloys, for example Nitinol, of magnesium or magnesium alloys, or of a bio-compatible plastic material, such as, for example, polyether ether ketone (PEEK) or poly-L-lactide acid (PLLA). In addition, the parts can be made of the same or of different materials from one another.

Figure 26C:
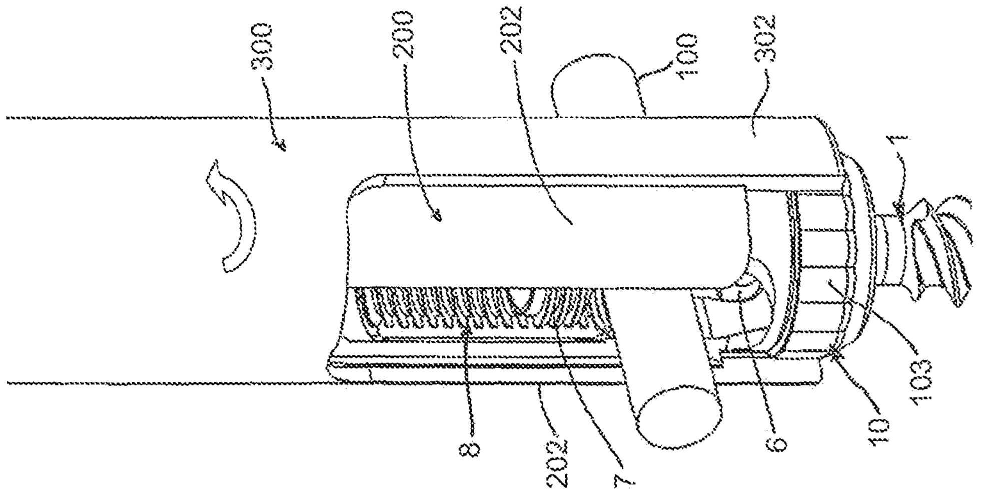
FIGS. 26*a* to 26*c* show steps of attaching and operating the instrument of FIGS. 20 to 25 in connection with the polyaxial bone anchoring device of FIGS. 1 to 3.
Figure 26B:
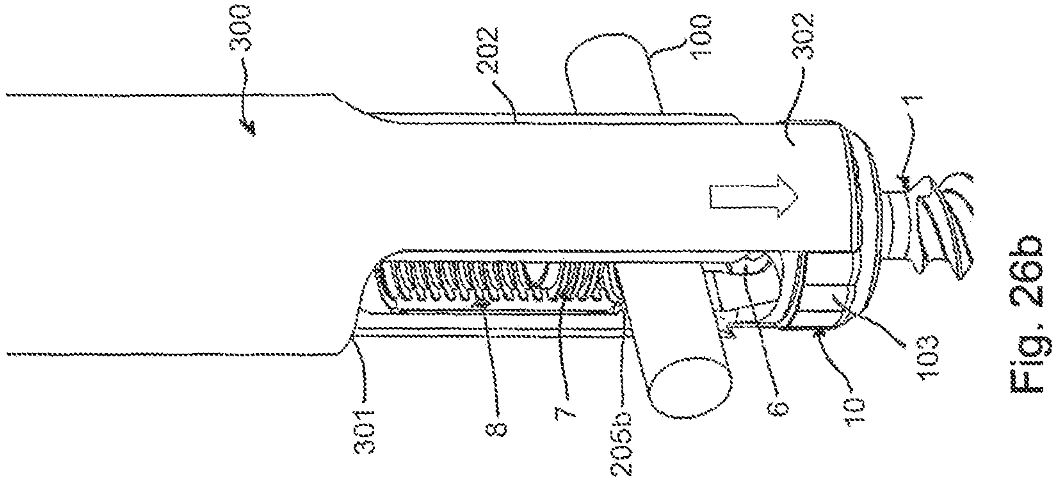
Figure 26A:
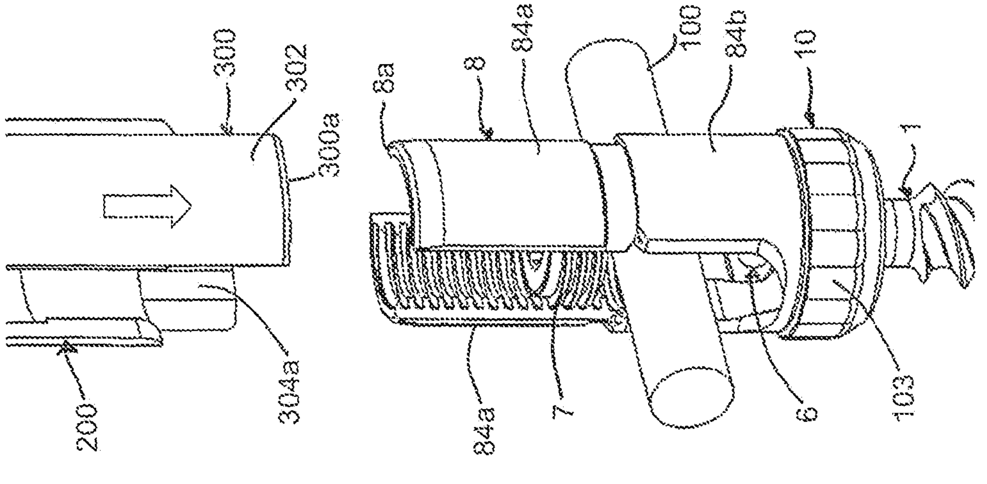

In FIGS. 26*a* to 26*c*, the steps of operating the instrument in connection with the polyaxial bone anchoring device according to the first embodiment are shown. As explained above, the polyaxial bone anchoring device can be pre-assembled. The rod 100 and the fixation member 7 may be inserted into the upper member 8. The instrument is assembled in a manner such that the arms 302 of the outer sleeve 300 overlap the arms 202 of the inner sleeve 200. One of the longitudinal edges of one arm 202 of the inner sleeve and one of the edges of the corresponding arm 302 of the outer sleeve are substantially aligned. As depicted in FIG. 26*a*, the instrument is placed onto the upper member 8 until the step 204*a* abuts against the projection 88*a* at the groove 88 and the thickened portions 205*b* of the arms 202 encompass the lower portion 84*b* of the legs 84 to rotationally fix the upper member 8. The arms 302 of the outer sleeve extend beneath the free end 200*a* of the inner sleeve 200, and the flat surface portions 304*a* engage the flat surface portions 103 of the lower member 10 in a form-fit manner (see FIG. 26*b*). As shown in FIG. 26*c*, the outer sleeve 300 is rotated and thereby rotates the lower member 10 so that the lower member 10 is further screwed onto the second portion 82 of the upper member 8.

Figures 27A, 27B, 27C, 27D:
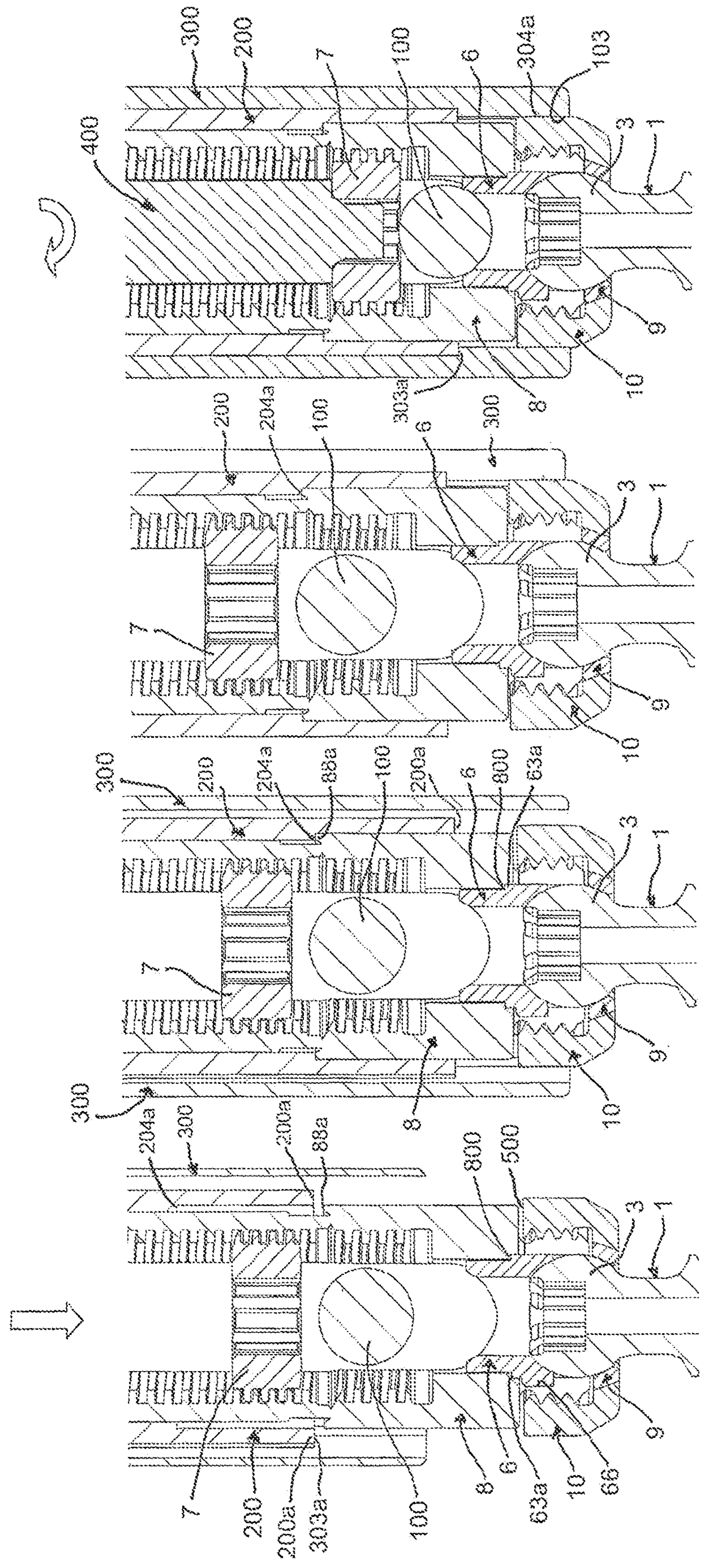
FIGS. 27*a* to 27*d* show further steps of operating the instrument of FIGS. 20 to 25 and the polyaxial bone anchoring device of FIGS. 1 to 3.

Turning now to FIGS. 27*a* to 27*d*, locking and unlocking of the head 3 will be explained. As shown in FIG. 27*a*, the lower member 10 is screwed onto the upper member 8 to such an extent that the head 3 is still pivotable relative to the receiving part. A gap 500 is provided between the first end 10*a* of the lower member 10 and the lower end 81*a* of the upper member 8. It shall be noted that the lower member 10 can be screwed to such an extent onto the second portion 82 of the upper member 8 that the head 3 is held either completely loose or that the head 3 is slightly clamped between the surfaces 92 of the insert member 9 and the surface 64 of the pressure member 6, so that the head is held by friction in an adjustable angular position. As the lower member 10 can be rotated in a step-less manner, the clamping force exerted onto the head 3 is adjustable. Hence, the lower member is in a first position in which the head is pivotable. The rod 100 and the fixation member 7 may already be inserted into the upper member 8. The instrument is placed onto the upper member 8.

As illustrated in FIG. 27*b*, the instrument is moved further downward until the upper member 8 is rotationally fixed by the inner sleeve 200 and the outer sleeve 300 engages the engagement structure of the lower member 10.

Then, as shown in FIG. 27*c*, the lower member 10 is rotated with the outer sleeve 300 so that the bottom of the lower member 10 with the ring-shaped insert 9 presses the head 3 against the pressure member 6. The pressure member 6 abuts with the shoulder 63*a* against the stop 800, which exerts a counter-force and prevents upward movement of the pressure member 6. In a second position of the lower member 10 relative to the upper member 8 the head 3 is locked. The rod 100 is freely movable in a direction along the rod axis and also in an axial direction along the central axis, only limited by the fixation member 7. In the second positon, there is still a gap 500 between the lower end 81*a* of the first portion 81 of the upper member 8 and the first end 10*a* of the lower member.

As shown in FIG. 27*d*, finally, the rod 100 is seated in the rod support surface 62 of the pressure member 6 and the fixation member 7 is tightened with a screwdriver 400 until it presses onto the rod 100, which in turn presses onto the pressure member 6 to finally lock the head 3 and the rod 100. The instrument can then be pulled away.

In the second position of the lower member 10, the instrument can be removed without loosening the locking of the head 3. Also, rotating the outer sleeve 300 in the opposite direction releases the locking of the head 3, so that the head 3 is pivotable.

Figure 28:
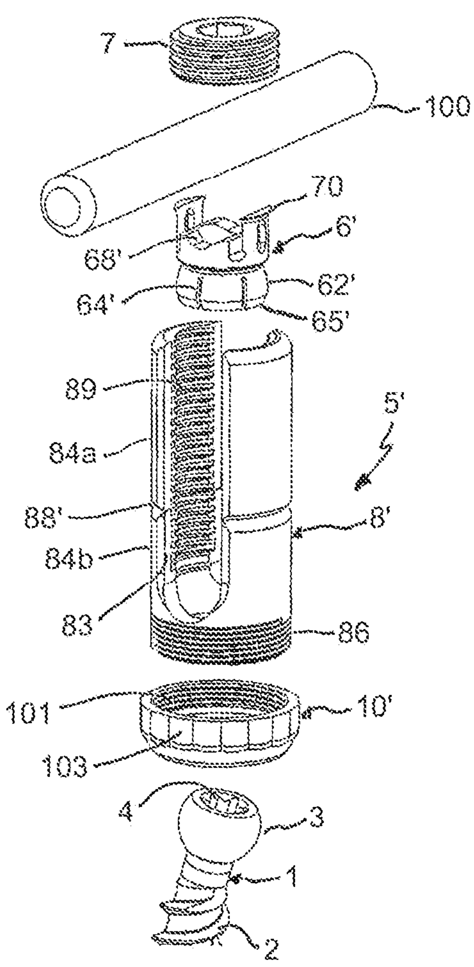
FIG. 28 shows a perspective exploded view of a second embodiment of a polyaxial bone anchoring device.
Figure 29:
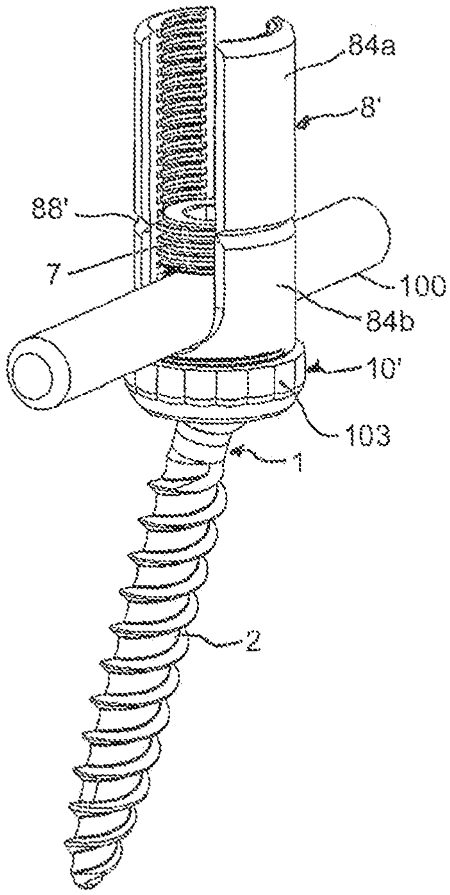
FIG. 29 shows a perspective view of the polyaxial bone anchoring device of FIG. 28 in an assembled state.
Figure 30:
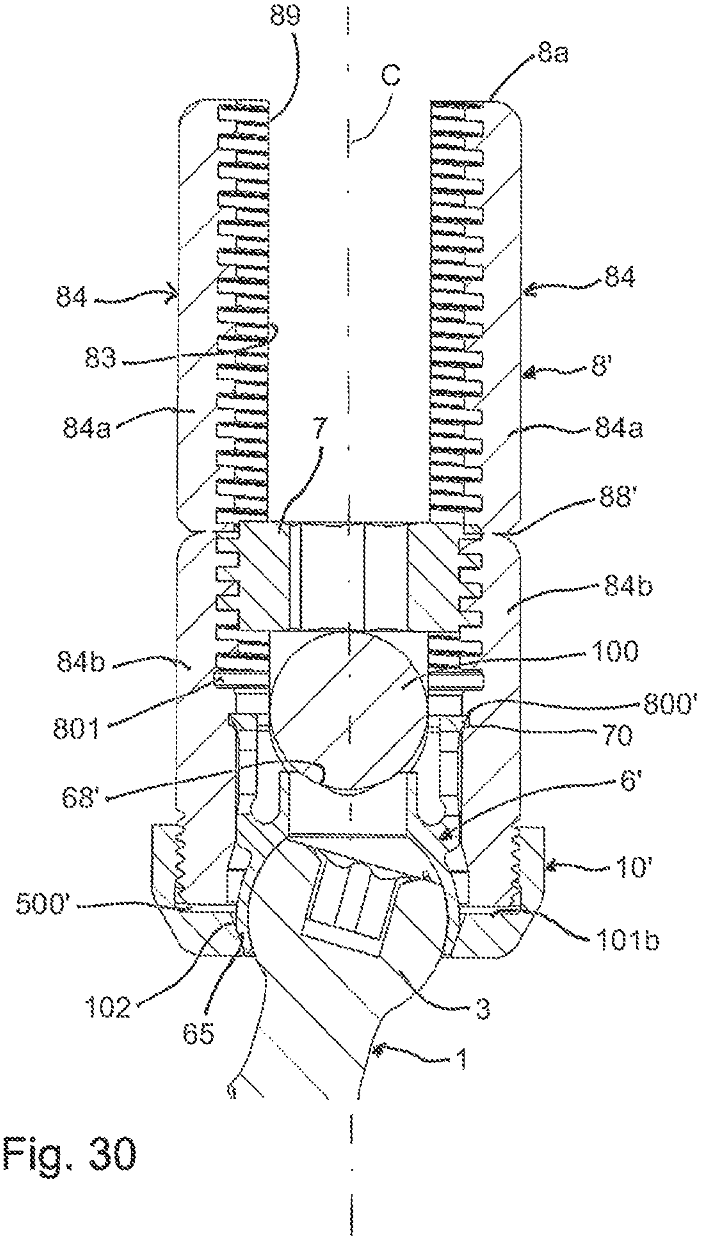
FIG. 30 shows a cross-sectional view of the polyaxial bone anchoring device of FIGS. 28 and 29, the cross-section taken in a plane perpendicular to an axis of an inserted rod.
Figure 31:
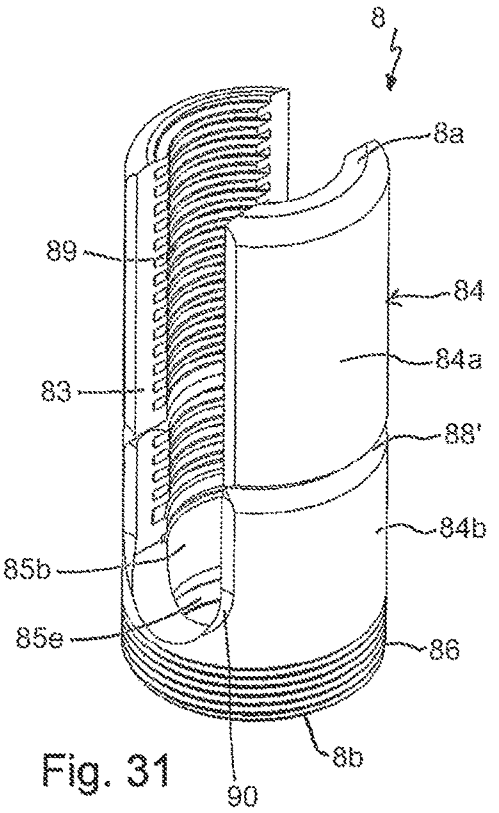
FIG. 31 shows a perspective view from a top of an upper member of a receiving part of the polyaxial bone anchoring device of FIGS. 28 to 30.
Figure 32:
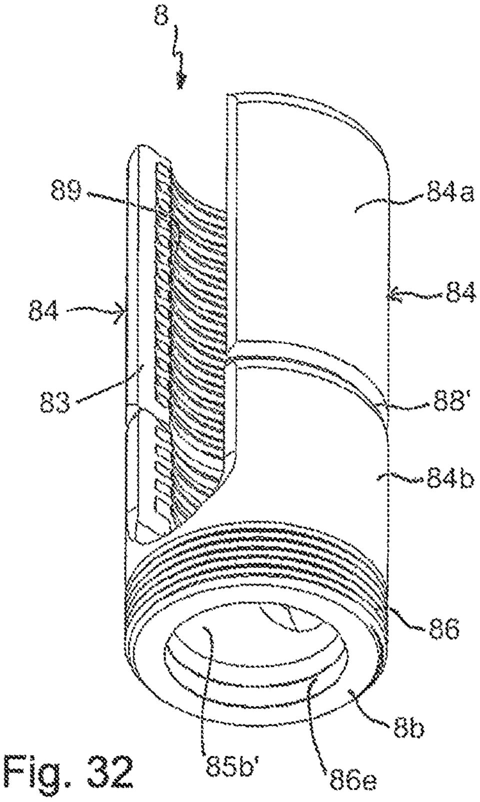
FIG. 32 shows a perspective view from a bottom of the upper member of FIG. 31.
Figure 33:
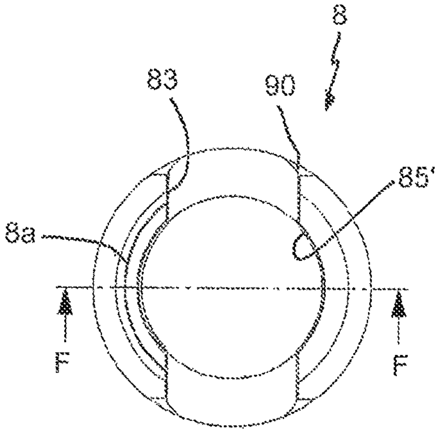
FIG. 33 shows a top view of the upper member of FIGS. 31 and 32.
Figure 34:
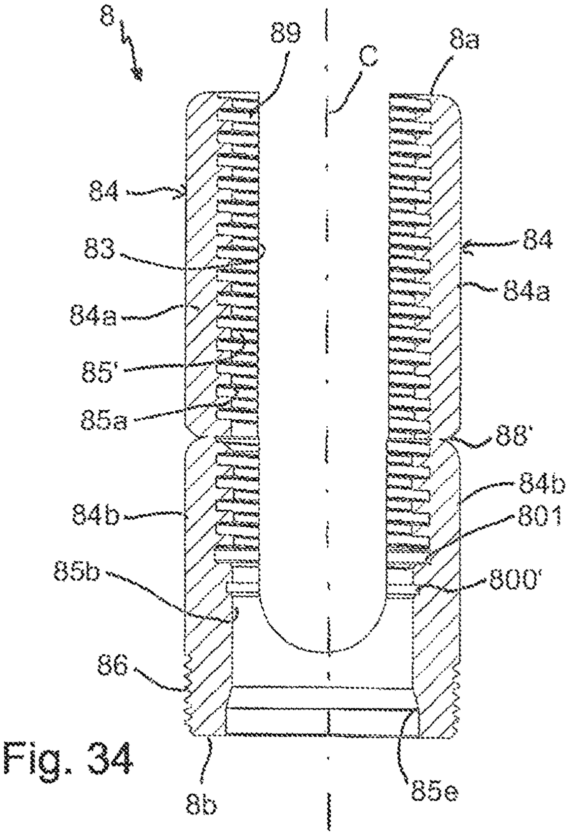
FIG. 34 shows a cross-sectional view of the upper member of FIGS. 31 to 33, the cross-section taken along line F-F in FIG. 33.
Figure 35:
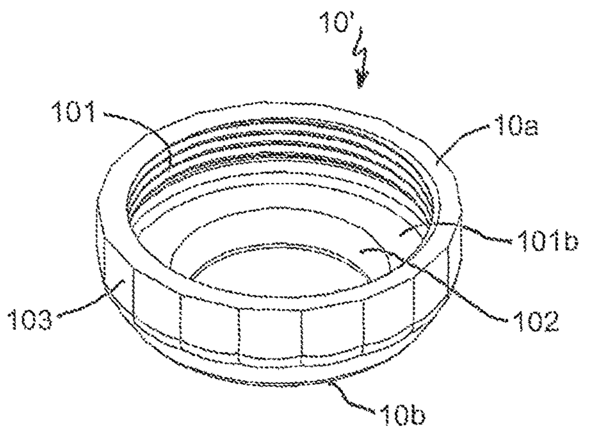
FIG. 35 shows a perspective view from a top of a lower member of the receiving part of the polyaxial bone anchoring device of FIGS. 28 to 30.
Figure 36:
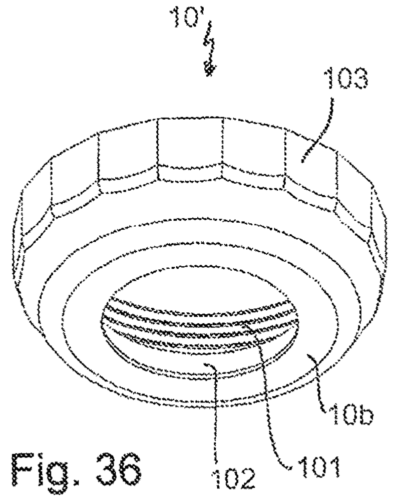
FIG. 36 shows a perspective view from a bottom of the lower member of FIG. 35.
Figure 37:
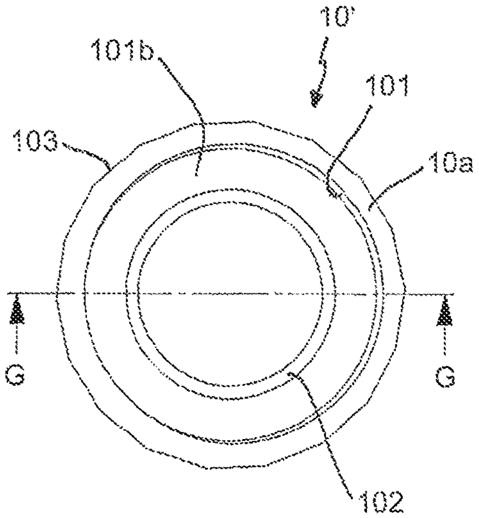
FIG. 37 shows a top view of the lower member of FIGS. 35 and 36.
Figure 38:
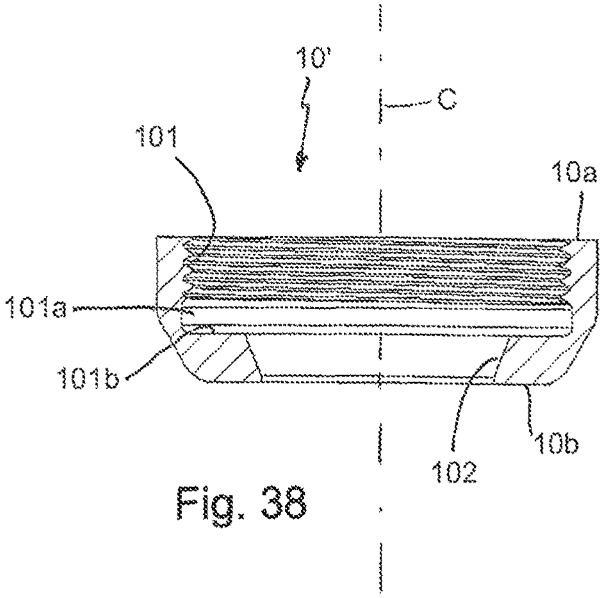
FIG. 38 shows a cross-sectional view of the lower member of FIGS. 35 to 37, the cross-section taken along line G-G in FIG. 37.
Figure 39:
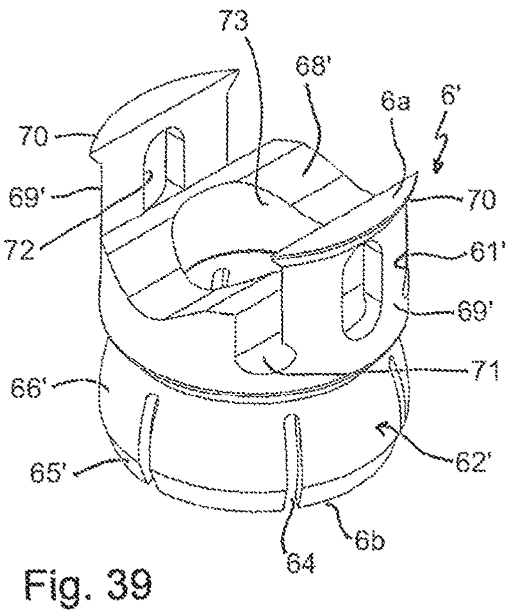
FIG. 39 shows a perspective view from a top of a pressure member of the polyaxial bone anchoring device of FIGS. 28 to 30.
Figure 40:
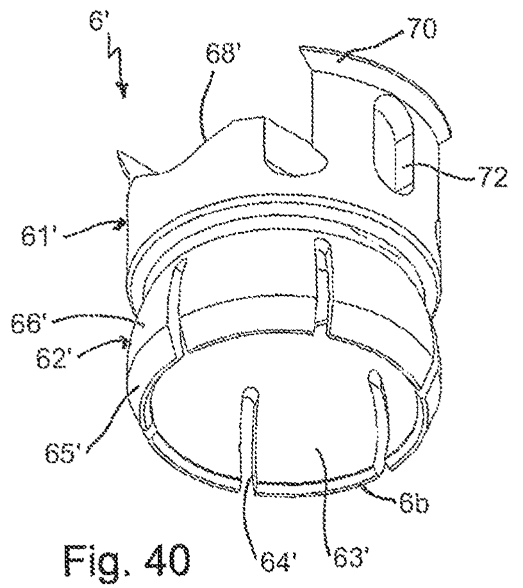
FIG. 40 shows a perspective view from a bottom of the pressure member of FIG. 39.
Figure 41:
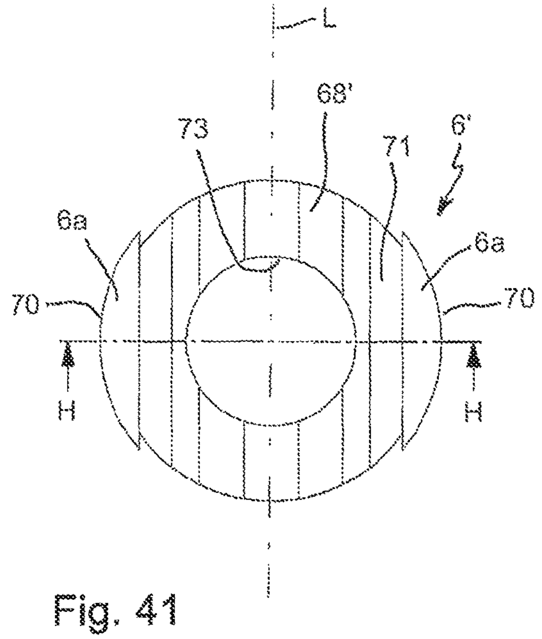
FIG. 41 shows a top view of the pressure member of FIGS. 39 and 40.
Figure 42:
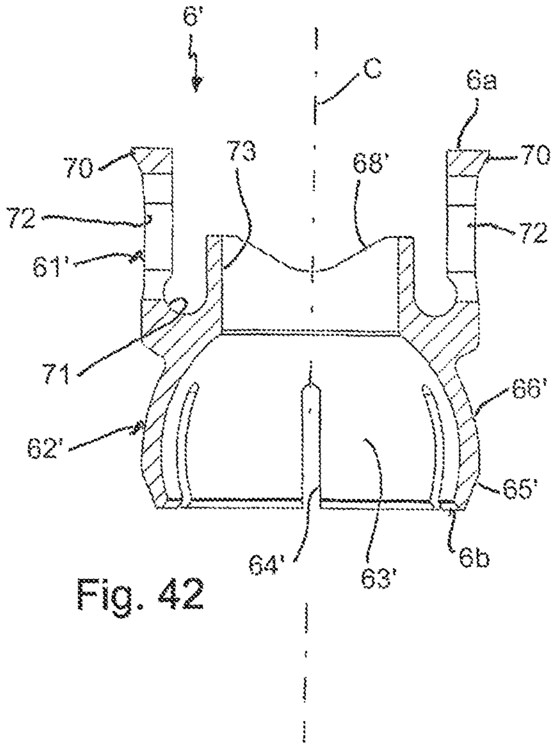
FIG. 42 shows a cross-sectional view of the pressure member of FIGS. 39 to 41, the cross-section taken along line H-H in FIG. 41.

FIGS. 28 to 30 depict a second embodiment of the polyaxial bone anchoring device. The description of parts and portions that are identical or similar to those of the first embodiment will not be repeated, and the reference numerals of those parts or portions are the same as in the first embodiment. The polyaxial bone anchoring device in FIGS.

28 to 30 differs from the polyaxial bone anchoring device according to the first embodiment in that it is designed as a bottom-loading polyaxial bone anchoring device, i.e., the head 3 of the bone anchoring element is insertable through a bottom end of the lower member 10'. The polyaxial bone anchoring device includes a receiving part 5' including an upper member 8' and a lower member 10'. Further, a pressure member 6' is provided in the upper member 8' and the lower member 10'.

Referring more in detail to FIGS. 31 to 34, the upper member 8' is a substantially cylindrical part between the first end **8*a* and the second end 8*b*. Adjacent to the second end 8*b*, an external thread 86 is provided at the outer surface that serves for connecting the lower member 10' to the upper member 8'. The passage 85' includes a first portion 85*a* adjacent to the first end 8*a* that extends to a distance above the bottom of the substantially U-shaped recess 83, and a second portion 85*b* with a slightly smaller diameter that widens towards the second end 8*b* in a widened portion 85*e*, to permit expansion of the pressure member 6' as explained below. At a distance from the bottom of the U-shaped recess 83, a circumferential groove 800' is provided in an inner wall of the legs 84, more specifically of a lower portion 84*b* of the legs 84. An upper edge of the groove 800' serves as a stop for the pressure member 6'. A lower edge of the groove 800' may be inclined to permit further downward movement of the pressure member 6'. An outer groove 88' that divides the legs 84 into an upper portion 84*a* and the lower portion 84*b***, and provides a break-off section, may have, for example, a V-shaped cross-section in a circumferential direction.

As depicted in FIGS. 35 to 38, the lower member 10' is a nut-like piece similar to the lower member of the first embodiment. The first portion 101 of the passage, which includes the internal thread, has a greater inner diameter so that it fits onto the external thread 86 of the upper member 8'. The second portion 102 of the passage also narrows towards the second end **10*b*. The second portion 102 is configured to receive a lower end of the pressure member 6' therein. Between the first portion 101 and the second portion 102, a flat annular surface 101*b*** is formed.

Turning now to FIGS. 39 to 42, the pressure member 6' will be described more in detail. The pressure member 6' includes an upper or first portion 61' with a first or upper end **6*a* and a lower or second portion 62' with a second or lower end 6*b*. The second portion 62' has a hollow interior 63' that may be substantially spherically-shaped to clamp the spherical head 3 therein. The second portion 62' has a plurality of slits 64' that are open at the lower end 6*b* and that extend through the second portion 62'. The number and dimensions of the slits 64' are such that the wall of the second portion 62' is flexible, more specifically that it can expand to snap onto the head 3 when the head 3 is inserted. An outer surface portion 65' adjacent to the lower end 6*b* of the pressure member 6' may be tapered, for example conically tapered. The outer surface portion 65' is configured to cooperate with the second portion 102 of the lower member 10' that narrows towards the second end 10*b*. Another outer surface portion 66' of the second portion 62' of the pressure member 6' may be spherically-shaped. Hence an overall shape of the second portion is cap-like. It shall be noted that the outer surface portions 65', 66'** can have any other shape.

The first portion 61' of the pressure member 6' may have a substantially cylindrical outer surface adjacent to the second portion 62'. In the embodiment shown, the second portion 62' is recessed with respect to the cylindrical first portion 61', however, any other shape may also be possible. A rod support surface 68' may be provided in the first portion 61' that is configured to support an inserted rod 100. The rod support surface 68' may have a V-shaped cross-section in a direction transverse to the central axis C to permit support of rods of different diameters. However, the rod support surface can also be flat or cylindrical, or can have any other shape.

The longitudinal axis L of the rod support surface 68' extends transverse to the central axis C. To the left and to the right of the rod support surface 68', upstanding legs 69' are formed that have a substantially flat inner surface and a substantially cylindrical outer surface. The upstanding legs 69' have outwardly directed portions 70 at their free ends, respectively, which are configured to engage the groove 800' of the upper member 8'. Between the rod support surface 68' and the upstanding legs 69', grooves 71 extending parallel to the rod support surface 68', are formed that render the upstanding legs 69' more flexible. The grooves 71 may have a circular segment-shaped cross-section. At the center of the upstanding legs 69', elongate through-holes 72 may be provided, the longitudinal axis of which is parallel to the central axis C. The through-holes 72 may be adapted to be engaged by pins (not shown) or other holding means to hold the pressure member 6' inside the upper member 8' and aligned with the U-shaped recess 83. To allow access to the head 3 with a driver or a tool, a coaxial bore 73 is provided in the pressure member 6'.

The dimensions of the pressure member 6' are such that the second portion 62' can expand in the enlarged portion **85*e* of the passage 85' of the upper member 8' when the head 3 of the bone anchoring element 1 is inserted. An outer diameter of the cylindrical first portion 61' is slightly smaller than an inner diameter of the second portion 85*b* of the passage 85' in the upper member 8' of the receiving part 5', such that the pressure member 6' can slide therein, wherein during insertion the flexible second portion 62' and the upstanding legs 69' may be slightly compressed until the second portion 62' is arranged in the accommodation space of the widening section 85*e***.

The bone anchoring device of the second embodiment may be pre-assembled in a manner such that the pressure member 6' is inserted into the upper member 8' and the lower member 10' is connected to the upper member 8'. The bone anchoring element 1 can thus be inserted from the bottom end **10*b* of the lower member 10' into the receiving part 5'**.

Figure 43D:
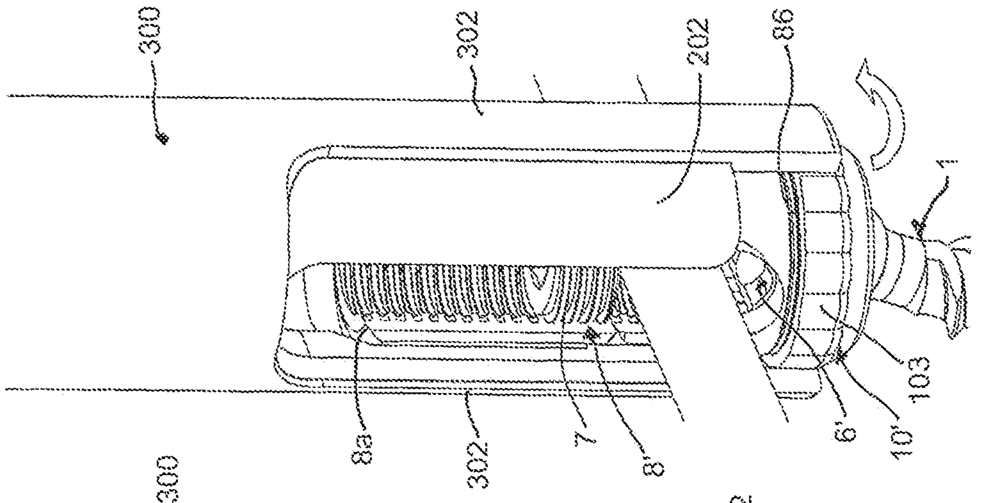
FIGS. 43*a* to 43*d* show steps of attaching and operating the instrument in connection with the polyaxial bone anchoring device according to FIGS. 28 to 30.
Figure 43C:
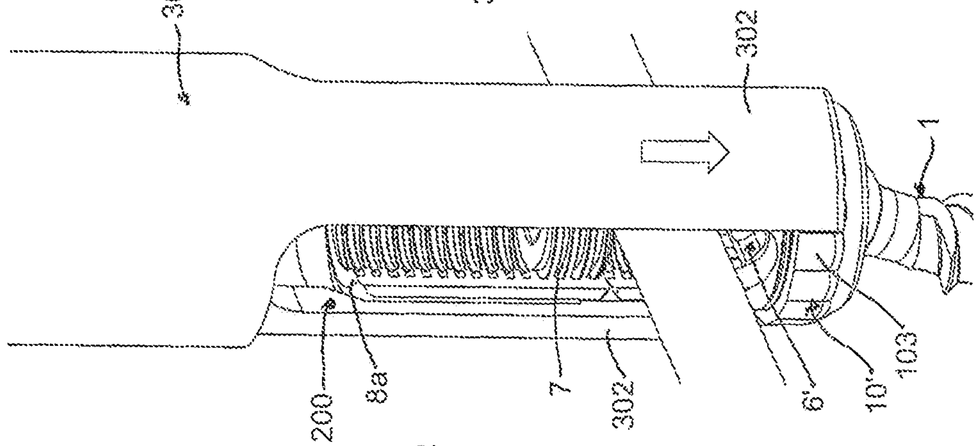
Figure 43B:
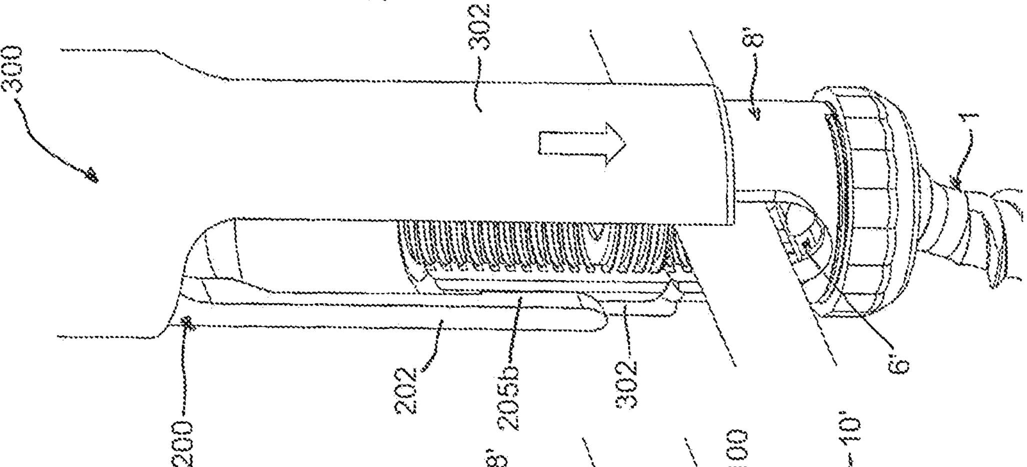
Figure 43A:
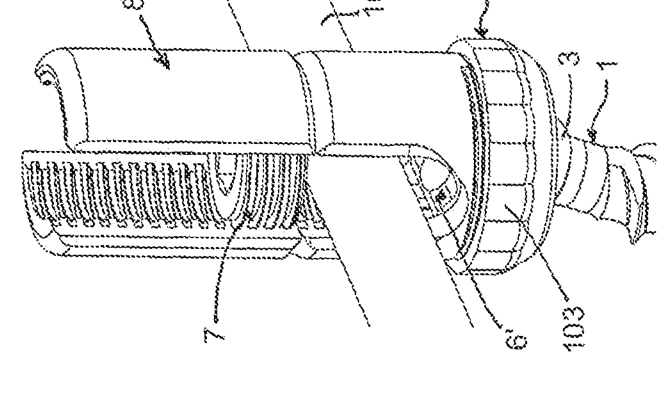

FIGS. **43*a* to 43*d* show steps of use of the bone anchoring device according to the second embodiment, in connection with the instrument. The instrument with the inner sleeve 200 and outer sleeve 300 as described in connection with FIGS. 20 to 25 can be used. The instrument can be attached to the assembled bone anchoring device with inserted rod 100 and fixation member 7 (see FIG. 43*a*) by downward movement of the respective front portions (see FIG. 43*b*), until the inner sleeve 200 engages the upper member 8' in a rotationally fixed manner and the outer sleeve 300 engages the engagement structure 103 on the outer surface of the lower member 10' (see FIG. 43*c*). For locking the head, the outer sleeve 300 is rotated to screw the lower member 10' towards the first end 8*a* of the upper member 8' (see FIG. 43*d***).

Figures 44A, 44B, 44C, 44D:
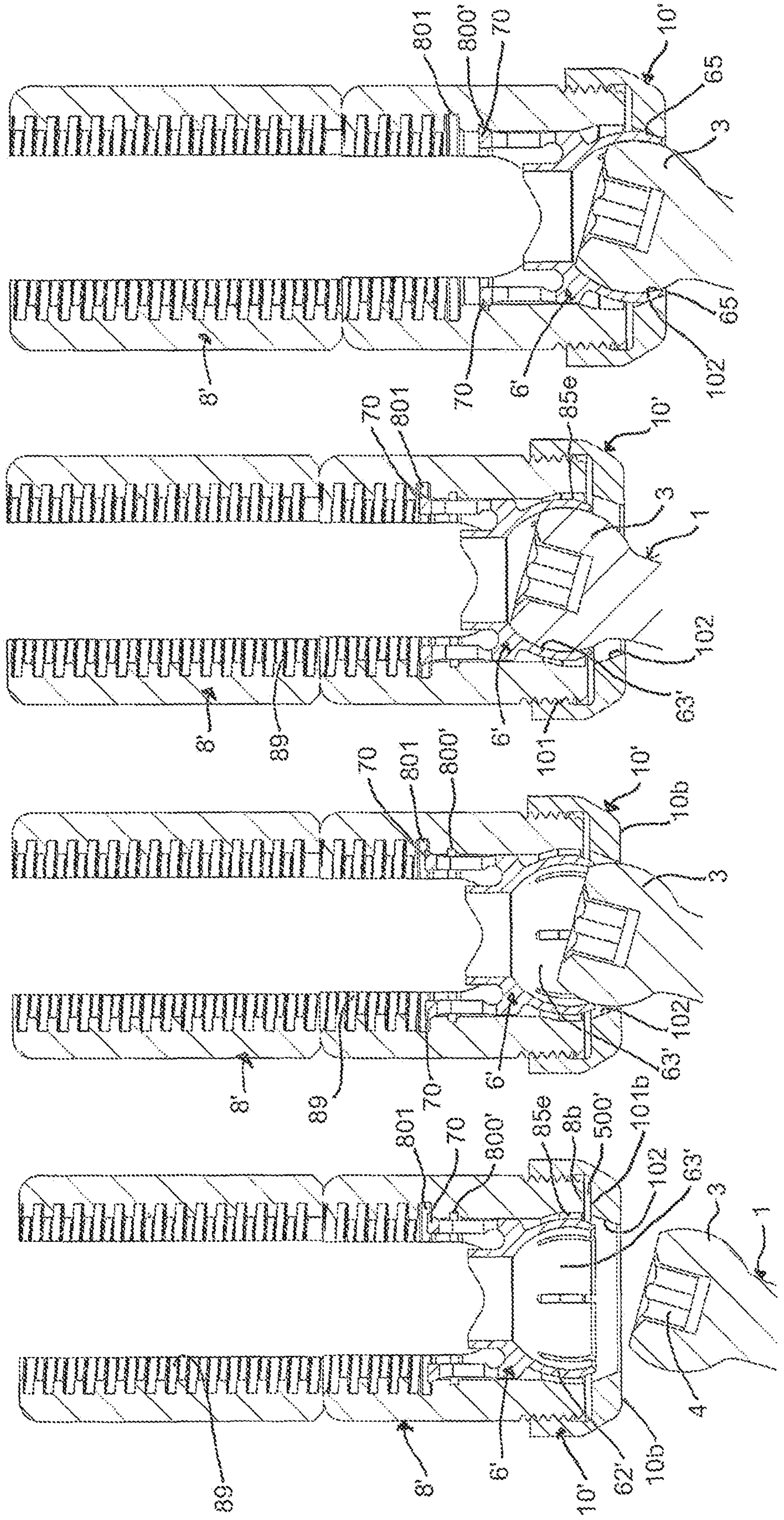
FIGS. 44*a* to 44*d* show cross-sectional views of steps of using the polyaxial bone anchoring device according to FIGS. 28 to 30.

Referring to FIGS. **44*a* to 44*d*, the assembly of the bone anchoring device will be explained in more detail. As shown in FIG. 44*a*, the pressure member 6' is in the upper member 8' in an insertion position, where the outwardly directed portions 70 extend into the undercut 801 at the lower end of the internal thread 89. The lower member 10' has been screwed onto the upper member 8' to such an extent that there is a gap 500' between the second end 8*b* of the upper member 8' and the bottom surface 101*a*** of the first portion

101 of the passage in the lower member 10'. The flexible portion 62' of the pressure member is at least partially located in the widening portion 85*e* of the passage 85' of the upper member 8' so that it can expand therein.

As depicted in FIG. 44*b*, the head 3 of the bone anchoring element 1 is inserted from the second end 10*b* of the lower member 10' and enters into the hollow interior 63' of the pressure member 6'. The head 3 pushes the pressure member 6' upward so that the outwardly directed portions 70 abut against the lowermost thread turn of the internal thread 89. The flexible second portion 62' of the pressure member snaps onto the head 3, as shown in FIG. 44*c*. Thereafter, the pressure member 6' can be moved downward until the outwardly extending portions 70 engage the groove 800'. The lowermost outer conical portion 65' of the pressure member 6' is moved into the second portion 102 of the passage in the lower member 10', thereby narrowing the lower opening (see FIG. 44*d*). In this pre-locking position, the pressure member 6' is prevented from moving upward and the head 3 is prevented from slipping out of the lower opening while the head 3 is still pivotable.

Figures 45A, 45B, 45C:
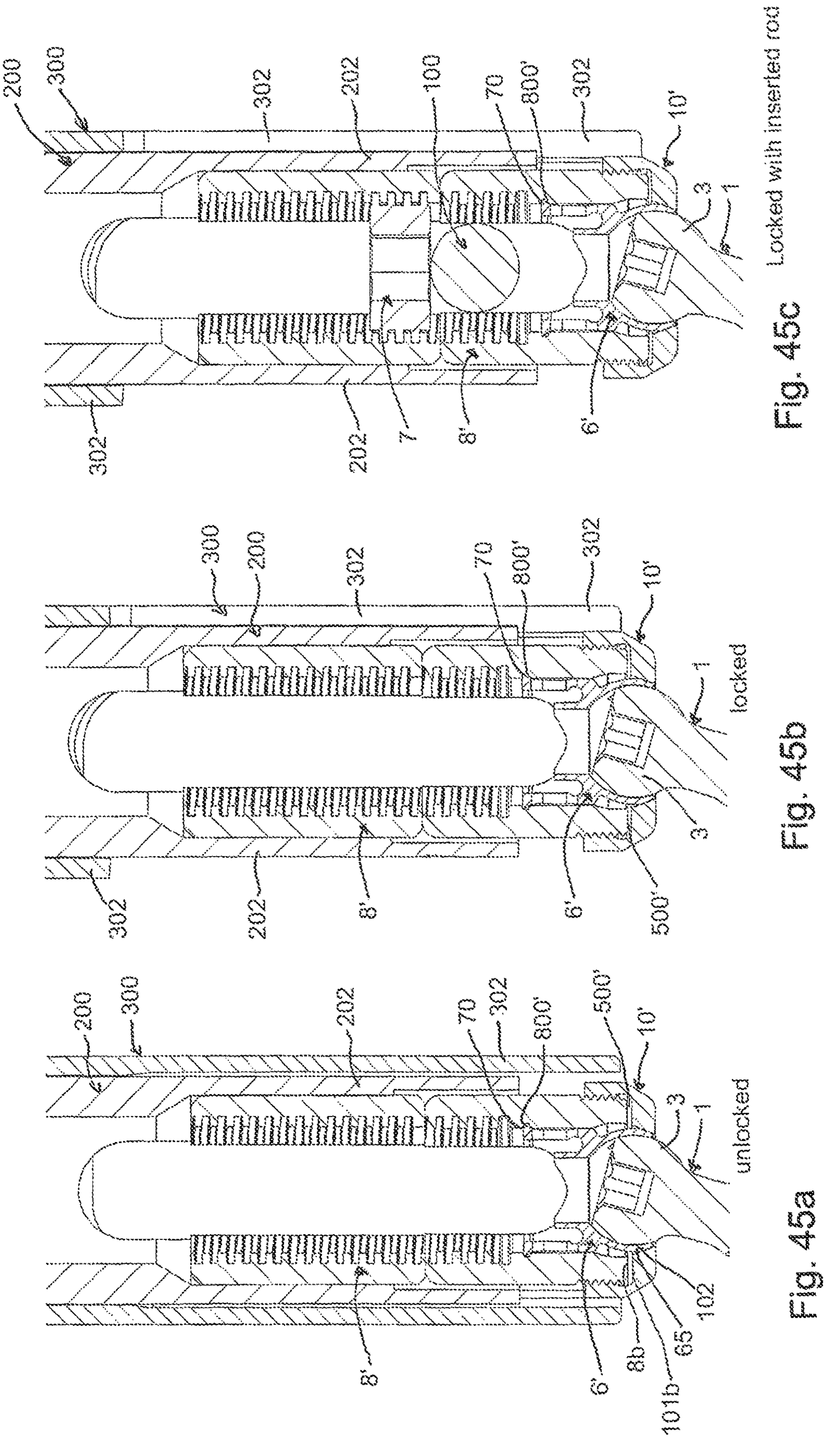
FIGS. 45*a* to 45*c* show cross-sectional views of operating states of the polyaxial bone anchoring device according to FIGS. 28 to 30.
Figure 1:
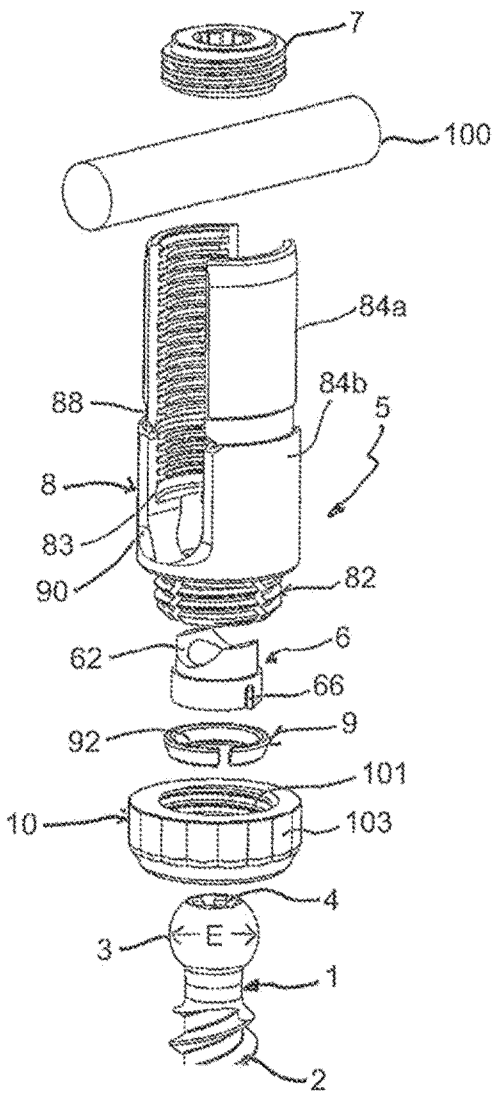
Figure 2:
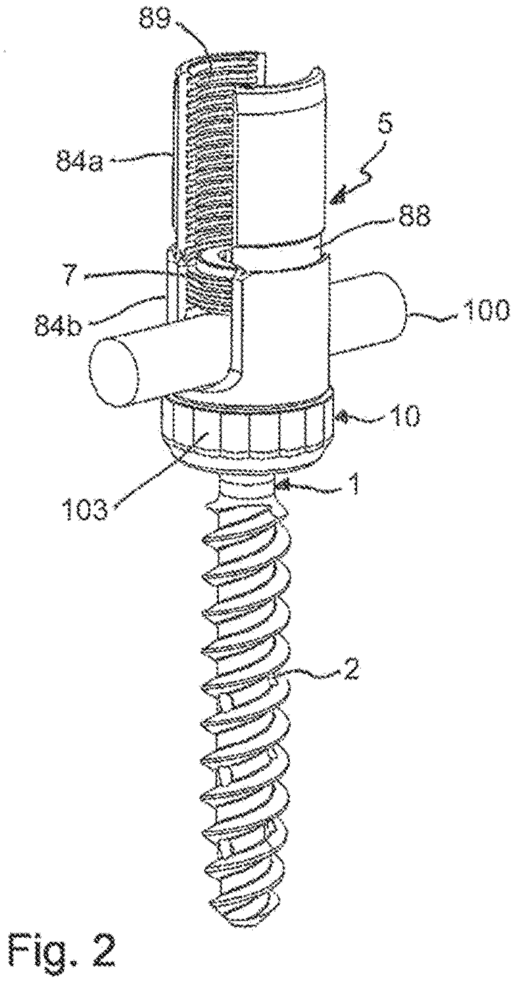
Figures 26A, 26B, 26C:
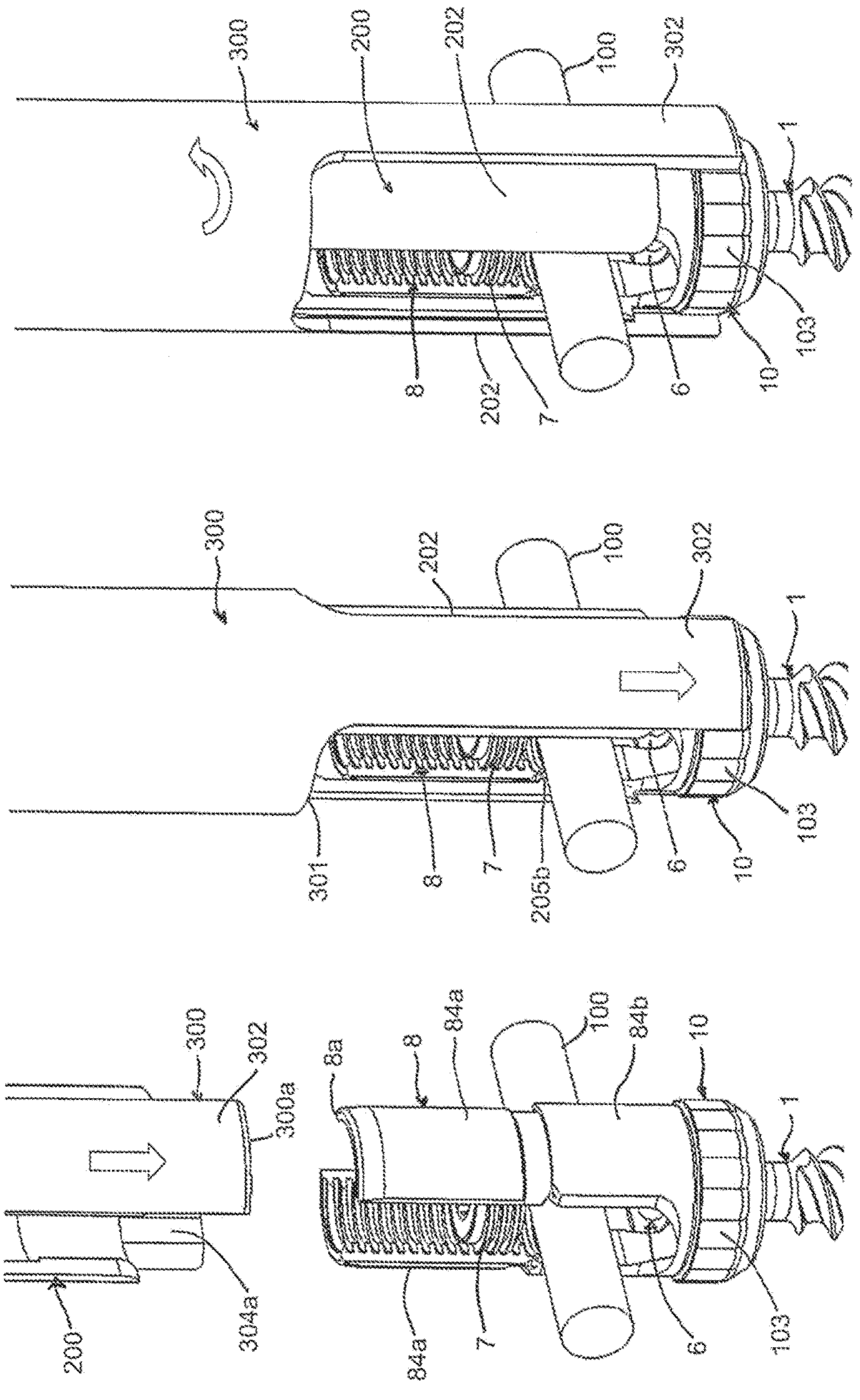

Steps of unlocking and locking the polyaxial bone anchoring device in FIGS. 28 to 30 using the instrument are shown in FIGS. 45*a* to 45*c*. As depicted in FIG. 45*a*, the head is unlocked, i.e., it is in a first position of the lower member 10' relative to the upper member 8', in which the head 3 is pivotable with respect to the components of the receiving part 5. The instrument is attached such that the inner sleeve 200 engages the upper member 8' and the outer sleeve engages the engagement structure at the lower member 10'. In FIG. 45*b*, the outer sleeve 300 has been rotated so that the lower member 10' is screwed further towards the first end 8*a* of the upper member 8', whereby the lower conical outer surface portion 65' of the pressure member 6' is pressed deeper into the second portion 102 of the passage of the lower member, and thereby the compression force by the flexible portion 62' onto the head 3 is increased until the lower member is in a second position in which the head 3 is locked. As the lower member 10' can be rotated in a step-less manner, the clamping force exerted onto the head 3 is adjustable. FIG. 45*c* shows the bone anchoring device and the instrument with an inserted rod 100 and a fixation member 7. In the second or locking position of the lower member 10', the gap 500' is smaller compared to the first or unlocking position.

In clinical use, at least two bone anchoring elements are inserted into, for example, the pedicles of adjacent vertebrae and the receiving parts are mounted onto the heads as described above. Thereafter, either the instrument is attached or the rod and the fixation member are inserted prior to attaching the instrument. With the bone anchoring device, a plurality of manipulations can be carried out by locking and unlocking the head, with or without the rod being placed into the receiving part.

Modifications of the above described embodiments are also conceivable. While the connection between the lower member and the upper member is shown to be a threaded connection, other types of connections could be used, for example a bayonet connection or others.

Other engagement structures of the lower member and the instrument may also be contemplated that provide a connection between the instrument and the lower member. Any firm connection that is able to transmit a force onto the lower member, such as any form fit-connection or friction-fit connection may be used.

Any instrument that holds the upper member rotationally fixed and permits moving of the lower member may be used.

The bone anchoring device according to other embodiments of the invention can be provided in further modified forms. For example, the head of the bone anchoring element can have any other shape, such as, for example, a cylindrical shape or a spherical shape with flattened sides, wherein a monoplanar device is provided that allows pivoting of the bone anchoring element in a single plane. The pressure member can also have a different shape.

The extended tabs on the receiving part can be omitted. In addition, in some embodiments, other kinds of fixation elements can also be used, for example, non-threaded locking elements that have an alternative advancement structure. In addition, all kinds of bone anchoring elements can be used, such as, for example, nails or bone anchors with barbs.

The various features of the embodiments can further be combined and/or interchanged to produce a variety of further embodiments.

While the present invention has been described in connection with certain exemplary embodiments, it is to be understood that the invention is not limited to the disclosed embodiments, but is instead intended to cover various modifications and equivalent arrangements included within the spirit and scope of the appended claims, and equivalents thereof.

What is claimed is:

1. A polyaxial bone anchoring device for coupling a rod to a bone, the bone anchoring device comprising:

a bone anchoring element comprising a shank and a head;

a receiving part comprising an upper member having a first end, a second end, a passage extending axially between the first and second ends, and a recess at the first end for receiving the rod, and a lower member separate from and connectable around at least part of the second end of the upper member; and a pressure member positionable at least partially in the upper member to exert pressure on the head;

wherein when the pressure member and the head are in the receiving part, the lower member is configured to assume a first position representing an axial position farthest away from the first end of the upper member where the lower member is attached to the upper member, wherein in the first position, the head is pivotable relative to the receiving part but is restricted from removal from the second end of the receiving part; and wherein the lower member is movable from the first position to a second position that is closer axially to the first end of the upper member, where an angular position of the head is locked relative to the receiving part while the recess for the rod remains sufficiently unobstructed for the rod to extend and move therethrough, and where at least part of the lower member is aligned axially with at least part of an end face at the second end of the upper member.

2. The polyaxial bone anchoring device of claim 1, wherein the pressure member is configured to abut a stop in the upper member when the head and the pressure member are in the receiving part and the lower member is at the second position.

3. The polyaxial bone anchoring device of claim 1, wherein a clamping force exerted on the head is greater when the lower member is at the second position than when the lower member is at the first position.

4. The polyaxial bone anchoring device of claim 1, wherein the lower member is movable from the first position to the second position with an instrument.

5. The polyaxial bone anchoring device of claim 4, wherein the lower member is configured to remain at the first position or at the second position without the instrument.

6. The polyaxial bone anchoring device of claim 1, wherein the lower member is further movable from the second position back to the first position.

7. The polyaxial bone anchoring device of claim 1, wherein the lower member is connectable to the upper member by means of a threaded connection.

8. The polyaxial bone anchoring device of claim 1, wherein the lower member comprises an outer engagement structure for engagement with an instrument to move the lower member from the first position to the second position.

9. The polyaxial bone anchoring device of claim 1, further comprising a fixation element for locking the rod in the recess.

10. The polyaxial bone anchoring device of claim 9, wherein the fixation element is configured to exert pressure on the pressure member via the rod.

11. The polyaxial bone anchoring device of claim 1, wherein when the lower member is connected to the upper member, the lower member defines an opening at an end opposite the first end of the upper member with an inner diameter that is greater than a largest width of the head of the bone anchoring element.

12. The polyaxial bone anchoring device of claim 11, further comprising an insert member configured to be inserted into the lower member to define an opening that is smaller than the largest width of the head.

13. The polyaxial bone anchoring device of claim 11, wherein the pressure member comprises an expandable portion for holding the head, and wherein a free end of the pressure member defines an opening configured to be smaller than the opening of the lower member.

14. The polyaxial bone anchoring device of claim 13, wherein the head of the bone anchoring element is insertable through the opening of the lower member into the receiving part.

15. The polyaxial bone anchoring device of claim 1, wherein the upper member comprises an inner wall portion with a spherical shape at or near the second end that is adapted to a spherical shape of the head.

16. The polyaxial bone anchoring device of claim 15, wherein the inner wall portion of the upper member is expandable to facilitate insertion of the head.

17. The polyaxial bone anchoring device of claim 1, wherein the head has a spherically-shaped outer surface portion.

18. The polyaxial bone anchoring device of claim 1, wherein the upper member comprises a lower surface and the lower member comprises an upper surface that faces the lower surface of the upper member when the lower member is connected to the upper member, and wherein a gap is formed between the upper and lower surfaces when the lower member is at the second position.

19. The polyaxial bone anchoring device of claim 1, wherein when the lower member is at the second position, another part of the lower member is at a same axial height as another part of the upper member.

20. A system comprising:

the polyaxial bone anchoring device of claim 1; and the rod;

wherein when the lower member is connected to the upper member with the pressure member and the head in the receiving part, the lower member is movable to the second position to lock the angular position of the head relative to the receiving part while the rod is in the recess and remains movable relative to the receiving part.

21. A system comprising:

the polyaxial bone anchoring device of claim 1; and an instrument comprising:

an outer sleeve configured to engage the lower member;

an inner sleeve positionable at least partially in the outer sleeve and configured to engage the upper member in a rotationally fixed manner;

wherein when the outer sleeve engages the lower member and the inner sleeve engages the upper member, the outer sleeve is movable relative to the inner sleeve to move the lower member relative to the upper member.

22. A method of coupling a rod to a bone using a polyaxial bone anchoring device comprising a bone anchoring element comprising a shank and a head, a receiving part comprising an upper member having a first end, a second end, a passage extending axially between the first and second ends, and a recess at the first end for receiving the rod, and a lower member separate from and connectable around at least part of the second end of the upper member, a pressure member positionable at least partially in the upper member to exert pressure on the head, and a fixation element, the method comprising:

anchoring the shank of the bone anchoring element to the bone;

pivoting the receiving part relative to the bone anchoring element when the pressure member and the head are in the receiving part and the lower member is connected to the upper member, wherein the lower member is configured to assume a first position representing an axial position farthest away from the first end of the upper member where the lower member is attached to the upper member, wherein in the first position, the head is pivotable relative to the receiving part but is restricted from removal from the second end of the receiving part;

moving the lower member closer axially to the first end of the upper member to a second position to lock an angular position of the head relative to the receiving part while the recess for the rod remains sufficiently unobstructed for the rod to extend and move therethrough, wherein when the lower member is at the second position, at least part of the lower member is aligned axially with at least part of an end face at the second end of the upper member;

adjusting the rod in the recess; and advancing the fixation member in the receiving part to fix the rod in the recess.

23. The method of claim 22, further comprising inserting the head of the bone anchoring element into the receiving part.

24. A polyaxial bone anchoring device for coupling a rod to a bone anchoring element, the bone anchoring device comprising:

a receiving part comprising an upper member having a first end, a second end, a passage extending axially between the first and second ends, and a recess at the first end for receiving the rod, and a lower member separate from and connectable around at least part of the second end of the upper member; and a pressure member positionable at least partially in the upper member to exert pressure on a head of the bone anchoring element, wherein when the pressure member is in the upper member, the upper member is configured to restrict movement of the pressure member towards the first end of the upper member while permitting movement of the pressure member away from the first end of the upper member;

wherein when the lower member is attached to the upper member with the pressure member in the receiving part, the lower member is movable relative to the upper member from a first position to a second position that is closer axially to the first end of the upper member to reduce a size of an opening defined at an end of the receiving part opposite the first end of the upper member;

wherein when the lower member is at the second position, at least part of the lower member is aligned axially with at least part of an end face at the second end of the upper member.

25. The polyaxial bone anchoring device of claim 1, wherein the lower member is further configured to assume a third position located axially between the first position and the second position, where the angular position of the head is held by friction but remains adjustable relative to the receiving part, while the recess for the rod remains sufficiently unobstructed for the rod to extend and move therethrough.

* * * * *

UNITED STATES PATENT AND TRADEMARK OFFICE

CERTIFICATE OF CORRECTION

PATENT NO. : 11,090,088 B2
APPLICATION NO. : 16/287896
DATED : August 17, 2021
INVENTOR(S) : Lutz Biedermann et al.

It is certified that error appears in the above-identified patent and that said Letters Patent is hereby corrected as shown below:

In the Drawings

Fig. 1, Sheet 1 of 16 Delete “Fig”, and
Insert -- Fig. --
Delete Drawing Sheet 1 and substitute therefore the Drawing Sheet, consisting of FIGs 1 &. 2, as shown on the attached page Fig. 26a, Sheet 7 of 16 Delete “Fig”, and
Insert -- Fig. --
Delete Drawing Sheet 7 and substitute therefore the Drawing Sheet, consisting of FIGs 26a, 26b, and 26c, as shown on the attached page Signed and Sealed this
Thirteenth Day of September, 2022

Katherine Kelly Vidal

Katherine Kelly Vidal
*Director of the United States Patent and Trademark Office*